US005468742A

United States Patent [19]
Petersen et al.

[11] Patent Number: 5,468,742
[45] Date of Patent: Nov. 21, 1995

[54] 8-VINYL- AND 9-ETHINYL-QUINOLONE-CARBOXYLIC ACIDS

[75] Inventors: Uwe Petersen, Leverkusen; Thomas Himmler, Odenthal; Thomas Schenke, Odenthal; Andreas Krebs, Odenthal; Klaus Grohe, Odenthal; Klaus-Dieter Bremm, Wuppertal; Karl G. Metzger, Wuppertal; Rainer Endermann, Wuppertal; Hans-Joachim Zeiler, Wuppertal, all of Germany

[73] Assignee: Bayer Aktiengesellschaft, Leverkusen, Germany

[21] Appl. No.: 146,569

[22] Filed: Nov. 1, 1993

Related U.S. Application Data

[60] Continuation-in-part of Ser. No. 62,495, May 14, 1993, abandoned, which is a division of Ser. No. 913,502, Jul. 14, 1992, abandoned.

[30] Foreign Application Priority Data

Jul. 19, 1991 [DE] Germany .......................... 41 23 918.0

[51] Int. Cl.$^6$ .......................... A61K 31/47; A61K 31/535; C07D 471/04; C07D 498/02

[52] U.S. Cl. .................. 514/187; 514/230.5; 514/235.2; 514/254; 514/300; 514/312; 544/105; 544/128; 544/363; 546/5; 546/14; 546/25; 546/113; 546/156; 560/43; 548/515

[58] Field of Search ................................. 546/5, 15, 113, 546/156; 514/187, 300, 312

[56] References Cited

U.S. PATENT DOCUMENTS

| | | | |
|---|---|---|---|
| 4,638,067 | 1/1987 | Culbertson et al. | 546/15 |
| 4,990,517 | 2/1991 | Petersen et al. | 514/300 |
| 5,047,538 | 9/1991 | Domagala et al. | 546/156 |
| 5,051,418 | 9/1991 | Schriewer et al. | 514/228.2 |
| 5,059,597 | 10/1991 | Petersen et al. | 546/156 |
| 5,116,834 | 5/1992 | Domagala et al. | 546/156 |
| 5,256,662 | 10/1993 | Domagala et al. | 514/249 |

Primary Examiner—Emily Bernhardt
Attorney, Agent, or Firm—William C. Gerstenzang; Sprung Horn Kramer & Woods

[57] ABSTRACT

The invention relates to new 8-vinyl- and 8-ethinylquinolonecarboxylic acids, process for their preparation, and antibacterial agents and feed additives containing them.

10 Claims, No Drawings

8-VINYL- AND 9-ETHINYL-QUINOLONE-CARBOXYLIC ACIDS

This application is a continuation-in-part of application Ser. No. 08/062,495, filed on May 14, 1993, now abandoned, which is a division of application Ser. No. 07/913,502, filed on Jul. 14, 1992, now abandoned.

The invention relates to new 8-vinyl- and 8-ethinylquinolonecarboxylic acids, processes for their preparation, and antibacterial agents and feed additives containing them.

It has already been disclosed that 8-alkyl-quinolonecarboxylic acids have antibacterial activity: 8-methylquinolonecarboxylic acids were described, for example, in EP 237,955 and JP 2,019,377, and 8-trifluoromethylcfuinolonecarboxylic acids were described in U.S. Pat. Nos. 4,780,468, 4,803,205, 4,933,335 and 5,047,538, the latter describing also 8-substitutions with unsaturated moieties.

It has now been found that the new compounds of the formula (I)

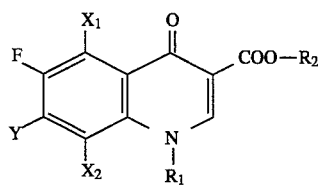

in which
- $R^1$ represents straight-chain or branched $C_1$–$C_4$-alkyl which is optionally substituted by hydroxyl, halogen or $C_1$–$C_3$-alkoxy, or represents optionally halogen- or $C_1$–$C_3$-alkyl-substituted $C_3$–$C_6$-cycloalkyl, $C_2$–$C_4$-alkenyl, furthermore represents $C_1$–$C_3$-alkoxy, amino, monoalkylamino having 1 to 3 C atoms, dialkylamino having 2 to 6 C atoms, or phenyl which is optionally monosubstituted to trisubstituted by halogen,
- $R^2$ represents hydrogen, alkyl having 1 to 4 carbon atoms or (5-methyl-2-oxo-1,3-dioxol-4-yl)-methyl,
- $X^1$ represents hydrogen, fluorine, chlorine, amino or methyl,
- $X^2$ represents

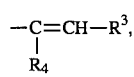

—C≡C—$R^5$ or —$CH_2$—CH=$CH_2$, where
- $R^3$ represents hydrogen, $C_1$–$C_3$-alkyl, $C_1$–$C_3$-alkoxy or alkoxymethyl having 1 to 3 C atoms in the alkoxy moiety,
- $R^4$ represents hydrogen or halogen and
- $R^5$ represents hydrogen, $C_1$–$C_6$-alkyl which is optionally monosubstituted to trisubstituted by halogen, or $C_2$–$C_3$-alkenyl, alkoxy having 1 to 3 C atoms, alkoxymethyl having 1 to 3 C atoms in the alkoxy moiety, halogen or trimethylsilyl, and
- Y represents

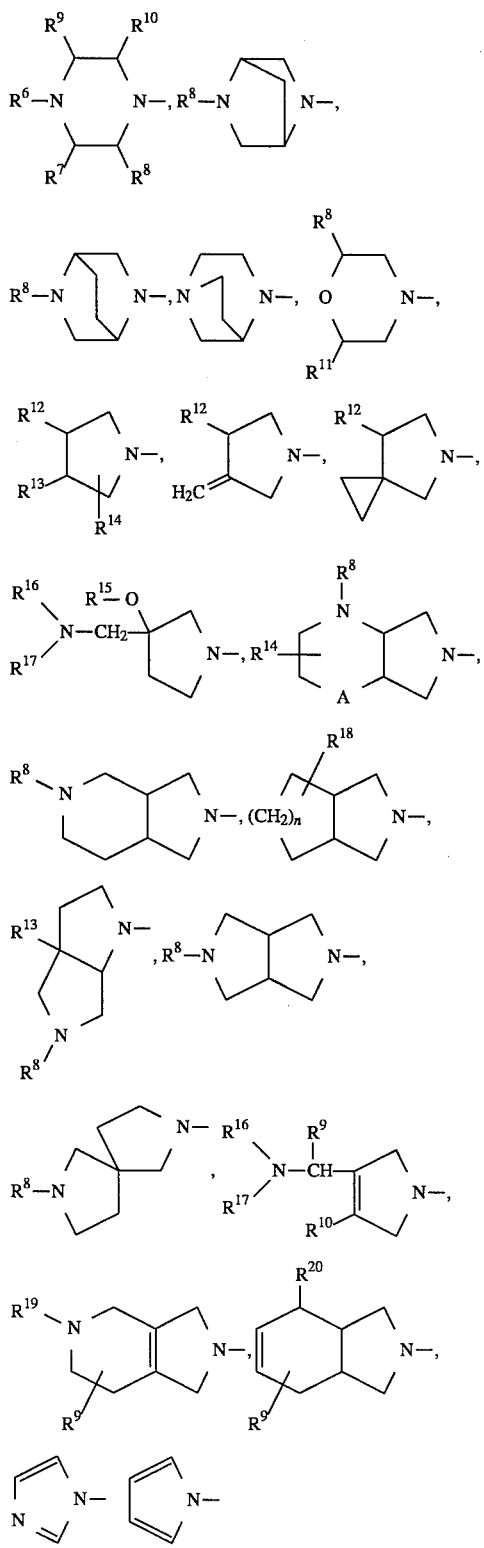

where
- $R^6$ represents hydrogen, optionally hydroxyl- or methoxy-substituted straight-chain or branched $C_1$–$C_4$-alkyl, cyclopropyl, oxoalkyl having 1 to 4 C atoms or acyl having 1 to 3 C atoms,
- $R^7$ represents hydrogen, methyl, phenyl, thienyl or pyridyl, $R^8$ represents hydrogen or methyl,
$R^9$ represents hydrogen or methyl,
$R^{10}$ represents hydrogen or methyl,
$R^{11}$ represents hydrogen, methyl or

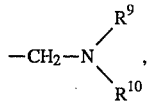

$R^{12}$ represents hydrogen, methyl, amino, optionally hydroxyl-substituted alkyl- or dialkylamino having 1 or 2 C atoms in the alkyl moiety, aminomethyl, aminoethyl, optionally hydroxyl-substituted alkyl- or dialkylaminomethyl having 1 or 2 C atoms in the alkyl moiety or 1-imidazolyl, $R^{13}$ represents hydrogen, hydroxyl, methoxy, methylthio or halogen, methyl or hydroxymethyl, $R^{14}$ represents hydrogen or methyl, $R^{15}$ represents hydrogen, methyl or ethyl, $R^{16}$ represents hydrogen, methyl or ethyl, $R^{17}$ represents hydrogen, methyl or ethyl, $R^{18}$ represents hydroxyl,

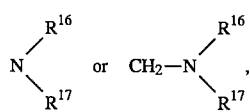

$R^{19}$ represents hydrogen, optionally hydroxyl-substituted $C_1$–$C_3$-alkyl, alkoxycarbonyl having 1 to 4 carbon atoms in the alkoxy moiety or $C_1$–$C_3$-acyl, $R^{20}$ represents hydrogen, hydroxyl,

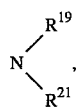

hydroxymethyl or

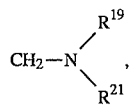

where
$R^{21}$ denotes hydrogen or methyl,
A represents $CH_2$, O or a direct bond and
n represents 1 or 2,
wherein
$X^2$ cannot be vinyl or ethinyl when $X^1$ and $R^2$ represents hydrogen, $R^1$ represents cyclopropyl or 2,4-difluorophenyl and Y represents 1-piperazinyl, 3-amino-1-pyrrolidinyl, 3-methylaminomethyl-1-pyrrolidinyl, 3-ethylaminomethyl-1-pyrrolidinyl, 2,5-diazabicyclo[2.2.1]hept-2-yl or 3-(1-aminoethyl)-1-pyrrolidinyl, and their pharmaceutically acceptable hydrates and acid addition salts as well as the alkali metal salts, alkaline earth metal salts, silver salts and guanidinium salts of the carboxylic acids on which they are based have a powerful antibacterial action.

They are therefore suitable as active compounds for human and veterinary medicine, veterinary medicine also including the treatment of fish for the therapy or prophylaxis of bacterial infections.

Preferred compounds of the formula (I) are those in which $R^1$ represents optionally hydroxyl-substituted $C_1$–$C_2$-alkyl, $C_3$–$C_5$-cycloalkyl, vinyl, amino, monoalkylamino having 1 to 2 C atoms, dialkylamino having 2 to 4 C atoms, or phenyl which is optionally monosubstituted or disubstituted by halogen, $R^2$ represents hydrogen, alkyl having 1 to 3 carbon atoms or (5-methyl-2-oxo-1,3-dioxol-4-yl)-methyl, $X^1$ represents hydrogen, fluorine, chlorine, amino or methyl, $X^2$ represents

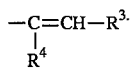

—C≡C—$R^5$ or —$CH_2$—CH=$CH_2$, where $R^3$ represents hydrogen, $C_1$–$C_2$-alkyl, methoxy or methoxymethyl, $R^4$ represents hydrogen and $R^5$ represents hydrogen, $C_1$–$C_4$-alkyl which is optionally monosubstituted to trisubstituted by fluorine, or $C_2$–$C_3$-alkenyl, methoxy or trimethylsilyl, and Y represents

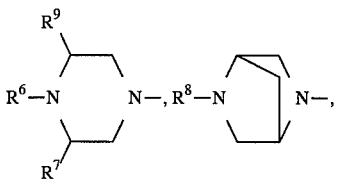

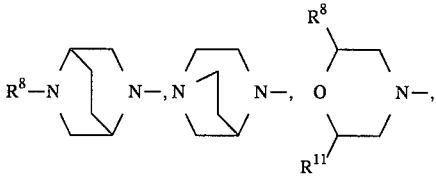

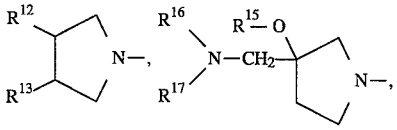

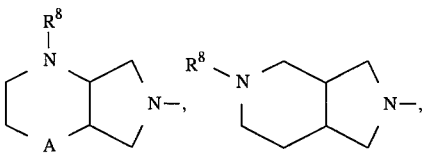

-continued

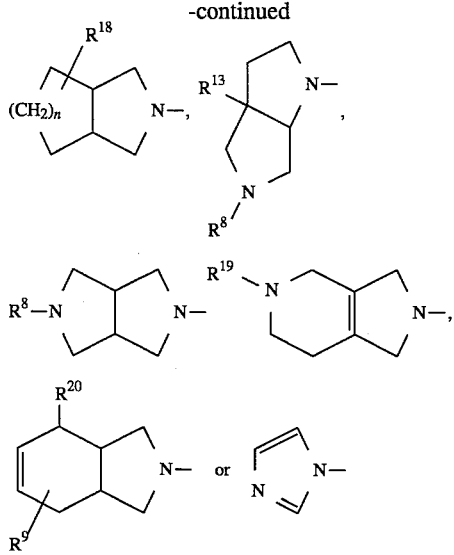

where
- R⁶ represents hydrogen, optionally hydroxyl-substituted straight-chain or branched $C_1$–$C_3$-alkyl or oxoalkyl having 1 to 4 C atoms,
- R⁷ represents hydrogen, methyl or phenyl,
- R⁸ represents hydrogen or methyl,
- R⁹ represents hydrogen or methyl,
- R¹¹ represents hydrogen, methyl or —$CH_2$—$NH_2$,
- R¹² represents hydrogen, methyl, amino, methylamino, dimethylamino, aminomethyl, methylaminomethyl or ethylaminomethyl,
- R¹³ represents hydrogen, hydroxyl, methoxy, fluorine, methyl or hydroxymethyl,
- R¹⁵ represents hydrogen or methyl,
- R¹⁶ represents hydrogen or methyl,
- R¹⁷ represents hydrogen or methyl,
- R¹⁸ represents

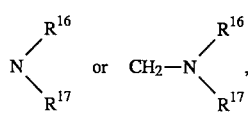

- R¹⁹ represents hydrogen, methyl or ethyl,
- R²⁰ represents

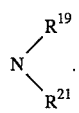

where
- R²¹ denotes hydrogen or methyl,
- A represents $CH_2$, O or a direct bond and
- n represents 1 or 2, wherein
X² cannot be vinyl or ethinyl when X¹ and R² represents hydrogen, R¹ represents cyclopropyl or 2,4-difluorophenyl and Y represents 1-piperazinyl, 3-amino-1-pyrrolidinyl, 3-methylaminomethyl-1-pyrrolidinyl, 3-ethylaminomethyl-1-pyrrolidinyl, 2,5-diazabicyclo[2.2.1]hept-2-yl or 3-(1-aminoethyl)-1-pyrrolidinyl.

Particularly preferred compounds of the formula (I) are those in which
- R¹ represents methyl, ethyl, cyclopropyl or phenyl which is optionally monosubstituted or disubstituted by fluorine,
- R² represents hydrogen, methyl or ethyl,
- X¹ represents hydrogen, fluorine, chlorine, amino or methyl,
- X² represents —CH=$CH_2$ or —C≡C—R⁵ where
  - R⁵ denotes hydrogen, $C_1$–$C_4$-alkyl, $C_2$–$C_3$-alkenyl or trimethylsilyl and
- Y represents

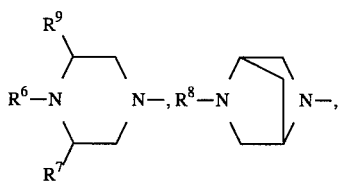

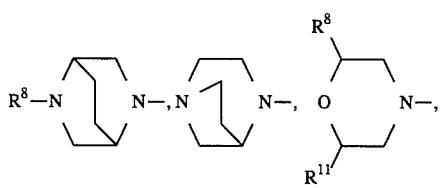

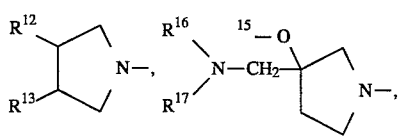

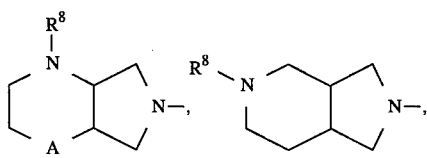

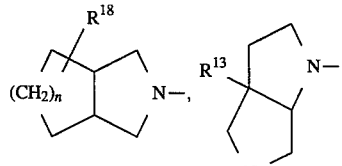

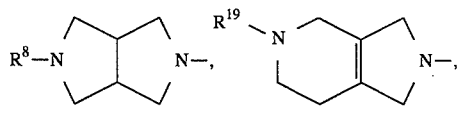

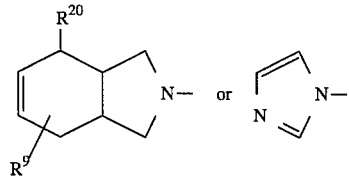

where
- R⁶ represents hydrogen, methyl, optionally hydroxyl-substituted ethyl, $R^7$ represents hydrogen or methyl,
$R^8$ represents hydrogen or methyl,
$R^9$ represents hydrogen or methyl,
$R^{11}$ represents hydrogen or —$CH_2$—$NH_2$,
$R^{12}$ represents hydrogen, methyl, amino, methylamino, aminomethyl or ethylaminomethyl,
$R^{13}$ represents hydrogen, hydroxyl or methoxy,
$R^{15}$ represents hydrogen or methyl,
$R^{16}$ represents hydrogen or methyl,
$R^{17}$ represents hydrogen or methyl,
$R^{18}$ represents

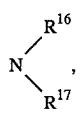

$R^{19}$ represents hydrogen or methyl,
$R^{20}$ represents

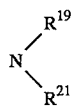

where
$R^{21}$ denotes hydrogen or methyl,
A represents $CH_2$, O or a direct bond and
n represents 1, wherein $X^2$ cannot be vinyl or ethinyl when $X^1$ and $R^2$ represents hydrogen, $R^1$ represents cyclopropyl or 2,4-difluorophenyl and Y represents 1-piperazinyl, 3-amino-1-pyrrolidinyl, 3-methylaminomethyl-1-pyrrolidinyl, 3-ethylaminomethyl-1-pyrrolidinyl, 2,5-diazabicyclo[2.2.1]hept-2-yl or 3-(1-aminoethyl)-1-pyrrolidinyl.

Furthermore, it has been found that the compounds of the formula (I) are obtained when a compound of the formula (II)

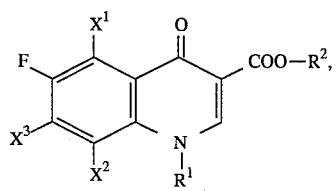

(II)

in which
$R^1$, $R^2$, $X^1$ and $X^2$ have the abovementioned meaning and
$X^3$ represents halogen, in particular fluorine or chlorine, is reacted with compounds of the formula (III)

Y—H  (III)

in which
Y has the abovementioned meaning, if appropriate in the presence of acid scavengers.

If, for example, 1-cyclopropyl-8-ethinyl-6,7-difluoro-1,4-dihydro-4-oxo-3-quinolinecarboxylic acid and 1-methylpiperazine are used as starting compounds, the course of the reaction can be represented by the following equation:

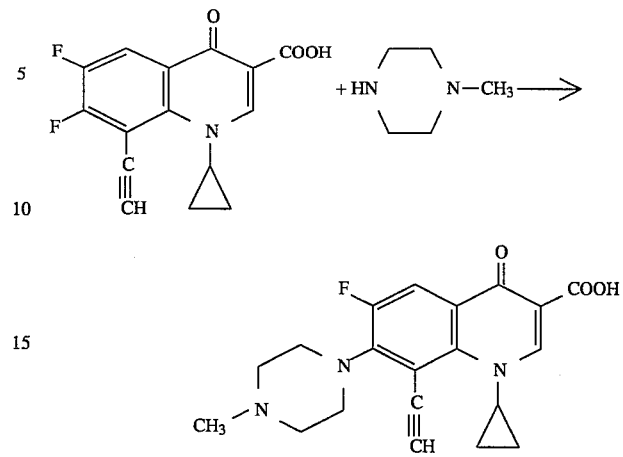

The 8-(1-chlorovinyl)-quinolonecarboxylic acids are also obtained by reacting the 8-ethinyl-quinolonecarboxylic acids with hydrochloric acid at temperatures from 10° C. to 100° C., preferably 20° C. to 60° C.

The compounds of the formula (II) can be prepared by reacting quinolinecarboxylic acid derivatives of the formula (IV)

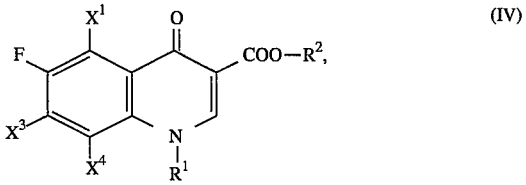

(IV)

in which
$R^1$, $R^2$, $X^1$ and $X^3$ have the abovementioned meaning and
$X^4$ represents halogen, in particular iodine, bromine or chlorine,
with organometal vinyl or alkinyl compounds of the formula (V)

M—$X^2$  (V)

in which
$X^2$ has the abovementioned meaning and
M represents $SnR'_3$, $ZnX'$, $B(OR'')_2$,
where
R' denotes $C_1$–$C_4$-alkyl,
R" denotes hydrogen or $C_1$–$C_4$-alkyl and
X' denotes bromine or chlorine,
in the presence of transition metal catalysts and eliminating any protective groups which may be present.

The organometal vinyl and alkinyl compounds which are required for the coupling reaction are either known or can be synthesised by methods known from the literature. For example, vinyl-trialkyltin compounds can be prepared from the corresponding vinyl iodides, vinyl bromides or vinyl chlorides by obtaining the vinyl-Grignard compounds by reaction with magnesium and reacting these compounds with a trialkyltin chloride to give the desired vinyltin derivatives.

Organometal alkinyl compounds can be prepared in a known manner, for example by metallating the 1-alkine with n-butyllithium, sec-butyllithium or tert.-butyllithium at temperatures between −20° and −78° C. in an aprotic solvent such as, for example, tetrahydrofuran, followed by reaction with a halometal compound such as, for example, zinc chloride, magnesium bromide, copper iodide or trialkyltin chloride. The reaction at −78° C. is preferred. Other possible solvents, apart from the preferred solvent tetrahydrofuran, are other ethers such as diethyl ether, dipropyl ether or tert.-butyl methyl ether, or mixtures of such ethers with aprotic, aliphatic or aromatic solvents such as n-hexane or toluene. The zinc chloride and trialkyltin derivatives are preferred with both the vinyl and the alkinyl derivatives. "Alkyl" in the trialkyltin compounds is understood as meaning $C_1$- to $C_6$-alkyl; methyl and n-butyl are preferred.

Trialkylvinyltin compounds can also be obtained by methods known from the literature, by hydrostannylation of alkines with trialkyltin hydrides in the presence of transition metal catalysts (J. Org. Chem. 55 (1990) 1857–1867).

The organometal vinyl and alkinyl compounds are reacted with 8-halogenoquinolonecarboxylic acid derivatives of the general formula (IV) by processes known in principle in the presence of a suitable catalyst. In this context, "halogen" represents iodine, bromine or chlorine; bromine and chlorine being preferred, bromine being particularly preferred.

Examples of suitable catalysts are transition metal compounds of the metals cobalt, ruthenium, rhodium, iridium, nickel, palladium or platinum. Compounds of the metals platinum, palladium and nickel are preferred, and palladium is particularly preferred. Such transition metals can be employed in the form of their salts such as, for example, in the form of $NiCl_2$, $PdCl_2$ or $Pd(OAc)_2$, or in the form of complexes with suitable ligands. The use of complexes is preferred. Ligands which are preferred are phosphines such as, for example, triphenylphosphine, tri(o-tolyl)phosphine, trimethylphosphine, tributylphosphine and tri(2-furyl)phosphine, triphenylphosphine being preferred. Preferred complex catalysts which may be mentioned are bis(triphenylphosphine)nickel(II) chloride, bis(triphenylphosphine)palladium(II) chloride, tris(triphenylphosphine)palladium(0) and tetrakis(triphenylphosphine)palladium(0).

The complex catalysts are employed in amounts of 0.1 to 20 mol %, relative to the 8-halogeno-quinolonecarboxylates employed; amounts of 0.5 to 10 mol % are preferred, and amounts of 1 to 5 mol % are very particularly preferred.

The coupling reactions are carried out in suitable inert solvents such as, for example, benzene, toluene, xylene, dimethylformamide, dimethylacetamide, dimethoxyethane or mixtures of such solvents; dimethylformamide and toluene are preferred. Before use, the solvents are dried and freed from air by known processes.

The coupling reactions are carried out at temperatures between 20° and 200° C.; temperatures between 50° and 180° C. are preferred.

The duration of the reaction depends on the reactivity of the educts and is generally between 2 and 40 hours; reaction times between 4 and 24 hours are preferred.

The reactions are carried out under a protective gas atmosphere. Suitable protective gases are inert gases such as, for example, helium, argon or nitrogen; nitrogen is preferred. The coupling reaction is generally carried out under atmospheric pressure. However, it is also possible, of course, to carry out the reaction under reduced or increased pressure.

Most of the amines of the formula (III) which are used as starting compounds are known. Chiral amines can be employed in the form of racemates as well as in the form of pure enantiomeric or pure diastereomeric compounds. Examples which may be mentioned are:

1-methylpiperazine,
1-ethylpiperazine,
1-(2-hydroxyethyl)-piperazine,
cis-2,6-dimethyl-piperazine,
cis-2,3-dimethyl-piperazine,
1,2-dimethylpiperazine,
1-cyclopropyt-piperazine,
2-phenyl-piperazine,
2-(4-pyridyl)-piperazine,
2-(2-thienyl)-piperazine,
1,4-diazabicyclo[3.2.1]octane,
8-methyl-3,8-diazabicyclo[3.2.1]octane dihydrochloride,
3-methyl-3,8-diazabicyclo[3.2.1]octane dihydrochloride,
2-methyl-2,5-diazabicyclo[2.2.1]heptane dihydrochloride,
2,5-diazabicyclo[2.2.2]octane dihydrochloride,
2-methyl-2,5-diazabicyclo[2.2.2]octane dihydrochloride,
1,4-diazabicyclo[3.1.1]heptane,
morpholine,
2,6-dimethyl-morpholine,
2-aminomethyl-morpholine,
2-tert.-butoxycarbonylaminomethyl-morpholine,
2-methylaminomethyl-morpholine,
2-dimethylaminomethyl-morpholine,
imidazole,
4-methyl-imidazole,
pyrrole,
3-aminomethyl-2,5-dihydro-pyrrole,
3-aminomethyl-4-methyl-2,5-dihydro-pyrrole,
3-(1-aminoethyl)-2,5-dihydro-pyrrole,
3-amino-azetidine,
3-tert.-butoxycarbonylamino-azetidine,
3-tert.-butoxycarbonylamino-2-methyl-azetidine,
3-tert.-butoxycarbonylamino-3-methyl-azetidine,
3-tert.-butoxycarbonylaminomethyl-azetidine,
pyrrolidine,
3-methylpyrrolidine,
3-tert.-butoxycarbonylamino-pyrrolidine,
3-(2,2-dimethyl-propylideneamino)-pyrrolidine,
3-methylamino-pyrrolidine,
3-dimethylamino-pyrrolidine,
3-aminomethyl-pyrrolidine,
3-tert.-butoxycarbonylaminomethyl-pyrrolidine,
4-chloro-3-tert.-butoxycarbonylaminomethyl-pyrrolidine,
3-tert.-butoxycarbonylaminomethyl-3-methyl-pyrrolidine,
3-tert.-butoxycarbonylamino-4-methyl-pyrrolidine,
3-tert.-butoxycarbonylaminomethyl-3-methoxy-pyrrolidine,
4-tert.-butoxycarbonylamino-2-methyl-pyrrolidine,
2-methyl-3-methylamino-pyrrolidine,
2-methyl-4-methylamino-pyrrolidine,
3-(2-hydroxyethylamino)-pyrrolidine,
3-hydroxy-pyrrolidine,
3-hydroxymethyl-pyrrolidine,
4-amino-3-hydroxy-pyrrolidine, 3-hydroxy-4-methylamino-pyrrolidine,
3-tert.-butoxycarbonylamino-4-methoxy-pyrrolidine,
3-methylaminomethyl-3-hydroxy-pyrrolidine,
3-dimethylaminomethyl-3-hydroxy-pyrrolidine,
3-diethylaminomethyl-3-hydroxy-pyrrolidine,
3-tert.-butylaminomethyl-3-hydroxy-pyrrolidine,
3-methylamino-4-hydroxymethyl-pyrrolidine,
4-methoxy-3-methylamino-pyrrolidine,
3-methoxy-3-methylaminomethyl-pyrrolidine,
3-amino-4-methoxy-2-methyl-pyrrolidine,
3-tert.-butoxycarbonylamino-3-methyl-pyrrolidine,
3-methyl-4-tert.-butoxycarbonylaminomethyl-pyrrolidine,
3-methoxy-4-tert.-butoxycarbonylaminomethyl-pyrrolidine,
3-(1-imidazolyl)-pyrrolidine,
6-hydroxy-3-azabicyclo[3.3.0]octane,
6-amino-3-azabicyclo[3.3.0]octane,
1-amino-3-azabicyclo[3.3.0]octane,
1-aminomethyl-3-azabicyclo[3.3.0]octane,
1-ethylaminomethyl-3-azabicyclo[3.3.0]octane,
6-amino-3-azabicyclo[4.3.0]nonane,
3-amino-4-methylene-pyrrolidine,
7-amino-5-azaspiro[2.4]heptane,
3,7-diazabicyclo[3.3.0]octane,
3-methyl-3,7-diazabicyclo[3.3.0]octane,
2,8-diazabicyclo[4.3.0]nonane,
2-methyl-2,8-diazabicyclo[4.3.0]nonane,
3-methyl-3,8-diazabicyclo[4.3.0]nonane,
2-oxa-5,8-diazabicyclo[4.3.0]nonane,
5-methyl-2-oxa-5,8-diazabicyclo[4.3.0]nonane,
2,7-diazabicyclo[3.3.0]octane,
2-methyl-2,7-diazabicyclo[3.3.0]octane,
3-methyl-2,7-diazabicyclo[3.3.0]octane,
4-methyl-2,7-diazabicyclo[3.3.0]octane,
tert.-butyl 5-methyl-2,7-diazabicyclo[3.3.0]octane,
7-methyl-2,7-diazabicyclo[3.3.0]octane,
8-methyl-2,7-diazabicyclo[3.3.0]octane,
7,8-dimethyl-2,7-diazabicyclo[3.3.0]octane,
2,3-dimethyl-2,7-diazabicyclo[3.3.0]octane,
2,8-dimethyl-2,7-diazabicyclo[3.3.0]octane,
1,4-diazatricyclo[6.2.0.0$^{2,6}$]decane,
1,4-diazatricyclo[6.3.0.0$^{2,6}$]undecane,
2,7-diazaspiro[4.4]nonane,
2-methyl-2,7-diazaspiro[4.4]nonane,
4-amino-1,3,3a,4,7,7a-hexahydroisoindole,
4-methylamino-1,3,3a,4,7,7a-hexahydroisoindole,
5-methyl-4-methylamino-1,3,3a,4,7,7a-hexahydroisoindole,
6-methyl-4-methylamino-1,3,3a,4,7,7a-hexahydroisoindole,
7-methyl-4-methylamino-1,3,3a,4,7,7a-hexahydroisoindole,
7a-methyl-4-methylamino-1,3,3a,4,7,7a-hexahydroisoindole,
6,7-dimethyl-4-methylamino-1,3,3a,4,7,7a-hexahydroisoindole,
4-dimethylamino-1,3,3a,4,7,7a-hexahydroisoindole,
4-ethylamino-1,3,3a,4,7,7a-hexahydroisoindole,
4-aminomethyl-1,3,3a,4,7,7a-hexahydroisoindole,
4-methylaminomethyl-1,3,3a,4,7,7a-hexahydroisoindole,
4-hydroxy-1,3,3a,4,7,7a-hexahydroisoindole,
2,3,4,5,6,7-hexahydro-1H-pyrrolo[3,4-c]pyridine,
5-methyl-2,3,4,5,6,7-hexahydro-1H-pyrrolo[3,4-c]pyridine,
5-ethyl-2,3,4,5,6,7-hexahydro-1H-pyrrolo[3,4-c]pyridine,
5-(tert.-butoxycarbonyl)-2,3,4,5,6,7-hexahydro-1H-pyrrolo[ 3,4-c]pyridine.

Most of the substituted 1,3,3a,4,7,7a-hexahydro-isoindoles are new. For example, they can be obtained by Diels-Alder reaction of dienes of the formula (1)

where $R^9$ has the abovementioned meaning and $R^{22}$ is either identical to $R^{20}$ or is a functional group which can be converted into $R^{20}$, with dienophiles of the formula (2)

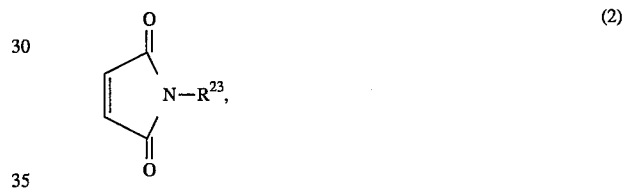

in which $R^{23}$ denotes hydrogen or a protective group such as trimethylsilyl, benzyl, $C_1$–$C_4$-alkylphenylmethyl, methoxybenzyl or benzylhydryl, followed by reduction of the carbonyl groups and, if appropriate, elimination of the protective group.

Suitable diluents for the Diels-Alder reaction are all inert organic solvents. These preferably include ethers, such as diisopropyl ether, di-n-butyl ether, dimethoxyethane, tetrahydrofuran and anisole, hydrocarbons such as, for example, hexane, methylcyclohexane, toluene, xylene and mesitylene, and halogenated hydrocarbons such as, for example, chloroform, 1,2-dichloroethane and chlorobenzene. However, the Diels-Alder reaction can also be carried out without a solvent.

The reaction temperatures can be varied within a substantial range. In general, the process is carried out between approximately −20° C. and +200° C., preferably between −20° C. and +150° C. The Diels-Alder reaction is usually carried out under atmospheric pressure. However, pressures of up to 1.5 GPa can also be used for accelerating the reaction.

Reduction of the carbonyl groups can be brought about using complex hydrides. Examples of hydrides which can be employed are lithium aluminum hydride, lithium borohydrides, lithium triethylborohydride, sodium-bis-[2-methoxyethoxy]-aluminiumhydride or sodium borohydride in the presence of Lewis acid catalysts such as chlorotrimethylsilane, boron trifluoride etherate or aluminium chloride.

Diluents which can be used are ethers such as, for example, diethyl ether, tetrahydrofuran, dioxane or dimethoxyethane, and hydrocarbons such as, for example, hexane, methylcyclohexane and toluene, and also mixtures of these.

The reaction temperatures can be varied in the range between −40° and +180° C., preferably between 0° and 140° C. The reduction is generally carried out under atmospheric pressure, but it can also be carried out under reduced pressure or under superatmospheric pressure.

The use of pressures between 100 and 1000 kPa is recommended so as to achieve higher reaction temperatures with low-boiling solvents.

The amount of complex hydrides employed in the reduction is at least stoichiometric. However, an excess of preferably between 30 and 300% is generally employed.

The elimination of a protective group which may be present is effected by the generally known methods of protective group chemistry (cf., for example, T. W. Greene, "Protective Groups in Organic Synthesis", John Wiley & Sons, New York 1981).

The starting substances of the formula (1) and (2) are known or can be prepared by generally known methods of organic chemistry [cf., for example, J. Am. Chem. Soc. 100, 5179 (1978), J. Org. Chem. 43, 2164 (1978), DE 3,927,115, J. Org. Chem. 40, 24 (1975)].

If, for example, 1-(tert.-butyloxycarbonylamino)-1,3-butadiene and maleimide are used as starting materials and lithium aluminium hydride as reducing agent, the course of the reaction can be represented by the following equation:

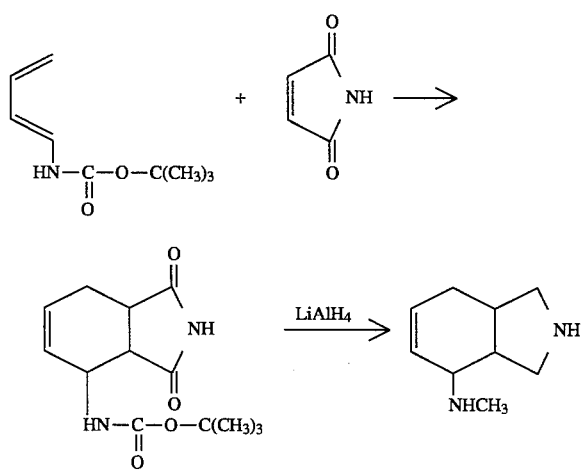

In a preferred embodiment of the preparation process, all stages can be carried out without isolation of the intermediates if a suitable solvent such as, for example, tetrahydrofuran, is used. If, for example, 1-(tert.-butyloxycarbonylamino)-1,3-pentadiene and N-trimethylsilyl-maleimide are used as starting materials, the course of the reaction can be represented by the following equation:

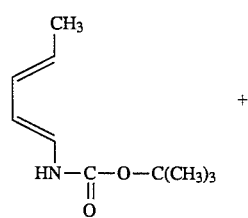

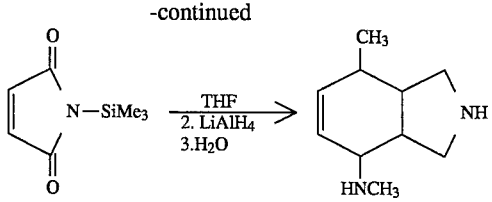

In this case, NMR spectroscopy demonstrates that all substituents on the 6-membered ring are in the cis-position relative to each other.

The reaction of (II) with (III), in which the compounds (III) can also be employed in the form of their salts such as, for example, the hydrochlorides, is preferably carried out in a diluent such as dimethyl sulphoxide, N,N-dimethylformamide, N-methylpyrrolidone, hexamethylphosphoric triamide, sulpholane, acetonitrile, water, an alcohol such as methanol, ethanol, n-propanol, isopropanol, glycol monomethyl ether or pyridine. Mixtures of these diluents can also be used.

Acid binders which can be used are all customary inorganic and organic acid-binding agents. These preferably include the alkali metal hydroxides, alkali metal carbonates, organic amines and amidines. The following substances which may be mentioned individually are particularly suitable: triethylamine, 1,4-diazabicyclo[2.2.2]octane (DABCO), 1,8-diazabicyclo[5.4.0]undec-7-ene (DBU) or excess amine (III).

The reaction temperatures can be varied within a substantial range. In general, the process is carried out at between approximately 20° and 200° C., preferably between 80° and 180° C.

The reaction can be carried out under atmospheric pressure, but also under increased pressure. In general, the pressures used are between approximately 1 and 100 bar, preferably between 1 and 10 bar.

When carrying out the process according to the invention, 1 to 15 moles, preferably 1 to 6 moles, of the compound (III) are employed per mole of the compound (II).

Free amino groups can be protected during the reaction by a suitable amino protective group, for example by the tert.-butoxycarbonyl radical, and set free by treatment with a suitable acid such as hydrochloric acid or trifluoroacetic acid, when the reaction has ended (see Houben-Weyl, Methoden der Organischen Chemie [Methods in Organic Chemistry], Volume E4, page 144 (1983); J. F .W. McOmie, Protective Groups in Organic Chemistry (1973), page 43).

The esters according to the invention are obtained by reaction of an alkali metal salt of the carboxylic acid on which they are based which, if appropriate, can be protected on the N atom by a protective group such as the tert.-butoxycarbonyl radical, with suitable halogenoalkyl derivatives in a solvent such as dimethylformamide, dimethylacetamide, N-methylpyrrolidone, dimethyl sulphoxide or tetramethylurea, at temperatures of approximately 0° to 100° C., preferably 0° to 50° C.

The acid addition salts of the compounds according to the invention are prepared in the customary manner, for example by dissolving the betaine in a sufficient amount of aqueous acid and precipitating the salt with an organic solvent, which is miscible with water, such as methanol, ethanol, acetone or acetonitrile. It is also possible to heat equivalent amounts of betaine and acid in water or an alcohol such as glycol monomethyl ether and subsequently to evaporate the mixture to dryness or filter off the precipitated salt with suction. Pharmaceutically acceptable salts are, for example, the salts of hydrochloric acid, sulphuric acid, acetic acid, glycolic acid, lactic acid, succinic acid, citric acid, tartaric acid, methanesulphonic acid, 4-toluenesulphonic acid, galacturonic acid, gluconic acid, embonic acid, glutamic acid or aspartic acid.

The alkali metal salts or alkaline earth metal salts of the carboxylic acids according to the invention are obtained, for example, by dissolving the betaine in a substoichiometric amount of alkali metal hydroxide solution or alkaline earth metal hydroxide solution, filtering off the undissolved betaine, and evaporating the filtrate to dryness. Pharmaceutically acceptable salts are sodium salts, potassium salts or calcium salts. The corresponding silver salts are obtained by reacting an alkali metal salt or alkaline earth metal salt with a suitable silver salt such as silver nitrate.

In addition to the active compounds mentioned in the examples, the active compounds listed in the table below can also be prepared, it being possible for these optionally chiral compounds to be present both as diastereomer mixtures or as the diastereomerically or enantiomerically pure compounds.

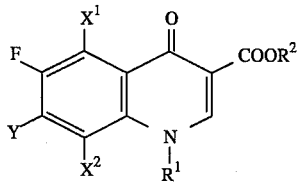

| $R^1$ | $R^2$ | $X^1$ | $X^2$ | Y |
|---|---|---|---|---|
|  | H | H | HC≡C— | 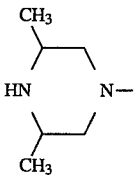 |
|  | H | H | HC≡C— | 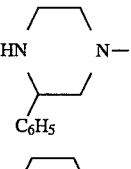 |
|  | H | H | HC≡C— | 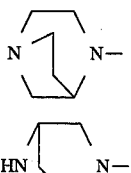 |
|  | H | H | HC≡C— | 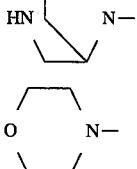 |
|  | H | H | HC≡C— | 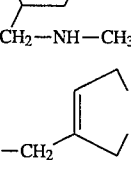 |
|  | H | H | HC≡C— | 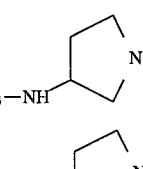 |
|  | H | H | HC≡C— | 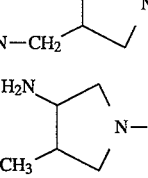 |
|  | H | H | HC≡C— |  |
|  | H | H | HC≡C— |  |

-continued

| R¹ | R² | X¹ | X² | Y |
|---|---|---|---|---|
| ▷ | H | H | HC≡C— | 3-amino-4-methoxypyrrolidin-1-yl |
| ▷ | H | H | HC≡C— | 3-(aminomethyl)-3-hydroxypyrrolidin-1-yl |
| ▷ | H | H | HC≡C— | 2,7-diazaspiro[4.4]nonan-2-yl |
| ▷ | H | H | HC≡C— | octahydropyrrolo[3,4-c]pyrrol-2-yl |
| ▷ | H | H | HC≡C— | octahydropyrrolo[3,4-b]pyrrol-1-yl |
| ▷ | H | H | HC≡C— | octahydropyrrolo[3,4-c]pyridin-2-yl |
| ▷ | H | H | HC≡C— | 4-amino-octahydrocyclopenta[c]pyrrol-2-yl |
| ▷ | H | H | HC≡C— | 4-amino-octahydroisoindol-2-yl |
| ▷ | C₂H₅ | H | HC≡C— | 4-(methylamino)-1,2,3,3a,4,7a-hexahydroisoindol-2-yl |
| ▷ | H | F | HC≡C— | 4-(methylamino)-1,2,3,3a,4,7a-hexahydroisoindol-2-yl |

-continued

| R¹ | R² | X¹ | X² | Y |
|---|---|---|---|---|
| cyclopropyl | H | NH₂ | HC≡C— | 4-(methylamino)-3a,4,7,7a-tetrahydroisoindol-2-yl |
| C₂H₅ | H | H | —C≡CH | 3-amino-pyrrolidin-1-yl |
| 2,4-difluorophenyl | H | H | —C≡CH | 4-amino-3a,4,7,7a-tetrahydroisoindol-2-yl |
| 2,4-difluorophenyl | H | H | —C≡CH | 4-(methylamino)-3a,4,7,7a-tetrahydroisoindol-2-yl |
| 2,4-difluorophenyl | H | H | —C≡C—CH₃ | 1,4-diazabicyclo[2.2.2] |
| cyclopropyl | H | H | F—C≡C— | 4-methylpiperazin-1-yl |
| cyclopropyl | H | H | F—C≡C— | 3-(methylaminomethyl)pyrrolidin-1-yl |
| cyclopropyl | H | H | F—C≡C— | 4-(methylamino)-3a,4,7,7a-tetrahydroisoindol-2-yl |
| cyclopropyl | H | H | CH₃O—C≡C— | 4-methylpiperazin-1-yl |
| cyclopropyl | H | H | CH₃O—C≡C— | 3-amino-pyrrolidin-1-yl |

-continued
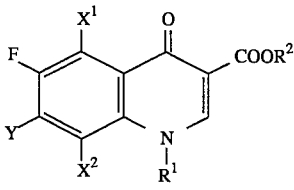
| R¹ | R² | X¹ | X² | Y |
|---|---|---|---|---|
|  | H | H | CF₃—C≡C— | 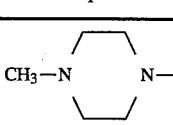 |
|  | H | H | CF₃—C≡C— | 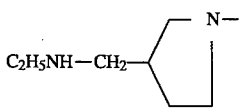 |
|  | H | H | CH₃O—CH₂—C≡C— | 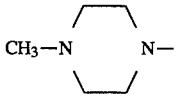 |
|  | H | H | CH₃O—CH₂—C≡C— | 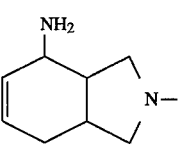 |
|  | H | H | CH₂=CH— | 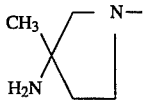 |
|  | H | H | CH₂=CH— | 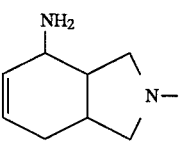 |
|  | H | H | CH₃O—CH=CH— | 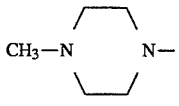 |
|  | H | H | CH₃O—CH=CH— | 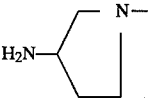 |
|  | H | H | CH₃O—CH₂—CH=CH— | 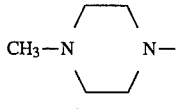 |
|  | H | H | CH₃O—CH₂—CH=CH— | 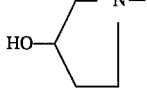 |
|  | H | H | CH₂=CH—CH₂— | 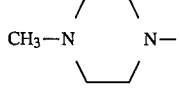 |

-continued

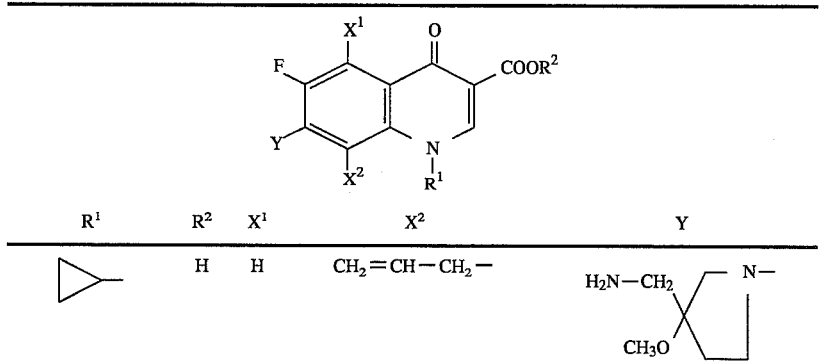

| R¹ | R² | X¹ | X² | Y |
|---|---|---|---|---|
| ▷ | H | H | $CH_2=CH-CH_2-$ | (H₂N-CH₂, CH₃O)-substituted N-pyrrolidinyl |

The compounds according to the invention are powerful antibiotics and show a broad antibacterial spectrum against Gram-positive and Gram-negative pathogens, in particular against enterobacteria, while having a low toxicity; in particular, they also act against those which are resistant to a range of antibiotics such as, for example, penicillins, cephalosporins, aminoglycosides, sulphonamides or tetracyclins.

These valuable properties allow them to be used as chemotherapeutic active compounds in medicine as well as preservatives of inorganic and organic materials, in particular all types of organic materials such as polymers, lubricants, colours, fibres, leather, paper and wood, as well as foodstuffs, and water.

The compounds according to the invention are active towards a very broad range of microorganisms. With their aid, it is possible to combat Gram-negative and Gram-positive bacteria and bacteria-like microorganisms, and to prevent, alleviate and/or cure the diseases caused by these pathogens.

The compounds according to the invention are distinguished by an improved action on resting and resistant microorganisms. In the case of quiescent bacteria, that is bacteria which do not show any detectable growth, the compounds act in concentrations far below those of previously known substances. This relates not only to the amount to be employed, but also to the speed of destruction. Such results were found in the case of Gram-positive and -negative bacteria, in particular in *Staphylococcus aureus, Pseudomonas aeruginosa, Enterococcus faecalis* and *Escherichia coli*.

Surprising improvements with regard to their action was also shown by the compounds according to the invention against bacteria which are classified as less sensitive to comparable substances, in particular resistant *Staphylococcus aureus, Escherichia coli, Pseudomonas aeruginosa* and *Enterococcus faecalis*.

By virtue of the powerful activity of the compounds according to the invention against bacteria and bacteria-like microorganisms, they are particularly suitable for the prophylaxis and chemotherapy of local and systemic infections in human and veterinary medicine which are caused by these pathogens.

Furthermore, the compounds are suitable for combating protozoonoses and helminthoses.

The compounds according to the invention can be used in a range of pharmaceutical preparations. Preferred pharmaceutical preparations which may be mentioned are tablets, coated tablets, capsules, pills, granules, suppositories, solutions, suspensions and emulsions, pastes, ointments, gels, crees, lotions, powders and sprays.

The minimum inhibitory concentrations (MIC) were determined on Iso-Sensitest agar (Oxoid) using the serial dilution method. For each test substance, a series of agar plates was prepared which contained concentrations of the active compound which decreased as the dilution was doubled. The agar plates were inoculated using a multipoint inoculator (Denley). The inocula used were overnight cultures of the pathogens which had previously been diluted to such an extent that each inoculation point contained approx. $10^4$ colony-forming units. The inoculated agar plates were incubated at 37° C., and growth of the pathogens was determined after approx. 20 hours. The MIC value (µg/ml) indicates the lowest concentration of active compound where no growth was discernible to the naked eye.

The table below lists the MIC values of some of the compounds according to the invention compared with ciprofloxacin.

TABLE

| | | MIC values | | | | | | | |
|---|---|---|---|---|---|---|---|---|---|
| | | Example | | | | | | | Cipro- |
| Test strain: | | 1 | 5 | 7 | 8 | 13 | 14 | 17 | floxacin |
| E. coli | Neumann | 0.02 | 0.02 | 0.13 | 0.25 | 0.13 | 0.02 | 0.03 | 0.02 |
| Micrococcus luteus | 9341 | | 0.5 | 1 | 2 | 0.25 | 8 | 1 | 2 |
| Staphylococcus aureus | ICB 25701 | 4 | 1 | 1 | 4 | 0.25 | 32 | 4 | 16 |
| | 1756 | 0.13 | 0.03 | 0.06 | 0.13 | 0.06 | 0.02 | 0.13 | 0.25 |
| | 133 | 0.13 | 0.13 | 0.06 | 0.13 | 0.06 | 0.02 | 0.13 | 0.25 |
| Enterococcus faecalis | 27101 | 0.25 | 0.13 | 0.25 | 0.5 | 0.13 | 1 | 0.25 | 0.5 |
| | 9790 | 0.25 | 0.13 | 0.25 | 1 | 0.13 | 1 | 0.25 | 0.5 |

TABLE-continued

| | | | | MIC values | | | | |
| | | | | Example | | | | Cipro- |
| Test strain: | | 1 | 5 | 7 | 8 | 13 | 14 | 17 | floxacin |
| --- | --- | --- | --- | --- | --- | --- | --- | --- | --- |
| *Acinetobacter calcoaceticus* | 14068 | 0.03 | 0.25 | 0.5 | 0.13 | 0.03 | 0.03 | 0.25 |

PREPARATION OF THE INTERMEDIATES

Example Z1

Ethyl 1-cyclopropyl-6,7-difluoro-1,4-dihydro-4-oxo-8-vinyl-3-quinolinecarboxylate 3.72 g of ethyl 8-bromo-1-cyclopropyl-6,7-difluoro-1,4-dihydro- 4-oxo-3-quinolinecarboxylate, 4.4 g of tributylvinyl stannan and 0.46 g of tetrakis(triphenylphosphine)palladium( 0) are refluxed in 40 ml of absolute toluene for 2 to 3 hours under a nitrogen atmosphere. The mixture is filtered under hot conditions, and the product which has precipitated at room temperature is filtered off with suction, washed with toluene and dried. 2.55 g of ethyl 1-cyclopropyl-6,7-difluoro-1,4-dihydro-4-oxo-8-vinyl-3-quinolinecarboxylate are obtained (79% of theory).

Melting point: 178°–179° C.

Example Z2

1-Cyclopropyl-6,7-difluoro-1,4-dihydro-4-oxo-8-vinyl-3-quinolinecarboxylic acid 0.9 g of ethyl 1-cyclopropyl-6,7-difluoro-1,4-dihydro-4-oxo- 8-vinyl-3-quinolinecarboxylate is refluxed for 4 hours in a mixture of 8 ml of glacial acetic acid, 0.6 ml of water and 0.2 ml of concentrated sulphuric acid. At reflux temperature, the reaction mixture is then treated with 10 ml of water. The solid is filtered off with suction at room temperature, washed with water and dried. 0.58 g of 1-cyclopropyl-6,7-difluoro-1,4-dihydro- 4-oxo-8-vinyl-3-quinolinecarboxylic acid (71% of theory) is obtained.

Melting point: 182°–184° C.

Example Z3

Ethyl 1-cyclopropyl-6,7-difluoro-1,4-dihydro-8-(trimethylsilyl-ethinyl)- 4-oxo-3-quinolinecarboxylate 22.2 g of ethyl 8-bromo-1-cyclopropyl-6,7-difluoro-1,4-dihydro- 4-oxo-3-quinolinecarboxylate, 30.2 g of tributylstannyl-trimethylsilyl-acetylene and 3.48 g of tetrakis(triphenylphosphine)palladium( 0) are refluxed for 3 hours in 300 ml of absolute toluene under a nitrogen atmosphere. After the reaction mixture has cooled to approx. −18° C., the solid is filtered off with suction, washed with toluene and dried. 18.8 g of ethyl 1-cyclopropyl- 6,7-difluoro-1,4-dihydro-8-(trimethylsilylethinyl)-4-oxo- 3-quinolinecarboxylate (80% of theory) are obtained.

Melting point: 171°–172° C.

Example Z4

Ethyl 1-cyclopropyl-8-ethinyl-6,7-difluoro-1,4-dihydro-4-oxo-3-quinolinecarboxylate 18.8 g of ethyl 1-cyclopropyl-6,7-difluoro-1,4-dihydro-8-(trimethylsilylethinyl)- 4-oxo-3-quinolinecarboxylate and 9.7 g of potassium fluoride are stirred for 3 hours at room temperature in a mixture of 300 ml of dimethylformamide, 200 ml of chloroform and 15 ml of water. The mixture is then filtered, the filtrate is treated with 120 ml of water, and the mixture is acidified with dilute aqueous hydrochloric acid. After extraction by shaking with chloroform, the organic phase is dried over sodium sulphate and concentrated. The residue obtained is recrystallised from methanol. In this way, 9 g of ethyl 1-cyclopropyl-8-ethinyl-6,7-difluoro-1,4-dihydro-4-oxo-3-quinolinecarboxylate (59% of theory) are obtained.

Melting point: 186°–187° C.

Example Z5

1-Cyclopropyl-8-ethinyl-6,7-difluoro-1,4-dihydro-4-oxo-3-quinolinecarboxylic acid 10.3 g of ethyl 1-cyclopropyl-8-ethinyl-6,7-difluoro-1,4-dihydro- 4-oxo-3-quinolinecarboxylate are refluxed for 4 hours in a mixture of 100 ml of glacial acetic acid, 8 ml of water and 3 ml of concentrated sulphuric acid. After cooling to room temperature, the solid is filtered off with suction, washed with water and dried. In this way, 5.7 g of 1-cyclopropyl-8-ethinyl-6,7-difluoro-1,4-dihydro- 4-oxo-3-quinolinecarboxylic acid (62% of theory) are obtained.

Melting point: 233° C.

Example Z6

Ethyl 1-cyclopropyl-6,7-difluoro-8-(1-hexinyl)-1,4-dihydro-4-oxo-3-quinolinecarboxylate 1.9 g of ethyl 8-bromo-1-cyclopropyl-6,7-difluoro-1,4-dihydro- 4-oxo-3-quinolinecarboxylate, 3.5 g of 1-tributylstannyl-hex-1-ine and 0.29 g of tetrakis(triphenylphosphine)palladium( 0) are refluxed for 8 hours in 20 ml of absolute toluene under a nitrogen atmosphere. The reaction mixture is concentrated, the residue is stirred with 30 ml of hexane, and the resulting solid is recrystallised from cyclohexane. 0.7 g of ethyl 1-cyclopropyl- 6,7-difluoro-8-(1-hexinyl)-1,4-dihydro-4-oxo-3-quinolinecarboxylate is obtained (36% of theory).

$^1$H NMR (200 MHz, CDCl$_3$): δ0.95 (t; 3 H), 1.1–1.7 (m; 11 H), 2.50 ( t; 2 H), 4.1–4.3 (m; 1 H), 4.38 (q; 2 H), 8.14 (dd; 1 H), 8.56 ( s; 1 H) ppm.

Example Z7

1-Cyclopropyl-6,7-difluoro-8-(1-hexinyl)-1,4-dihydro-4-oxo- 3-quinolinecarboxylic acid 0.7 g of ethyl 1-cyclopropyl-6,7-difluoro-8-(1-hexinyl)-1,4-dihydro-4-oxo-3-quinolinecarboxylate is refluxed for 3 hours in a mixture of 6 ml of glacial acetic acid, 0.5 ml of water and 0.1 ml of concentrated sulphuric acid. The reaction mixture is treated with 100 ml of water, and the solid is filtered off with suction and dried. 0.5 g of 1-cyclopropyl-6,7-difluoro-8-(1-hexinyl)- 1,4-dihydro-4-oxo-3-quinolinecarboxylic acid is obtained (85% of theory).

$^1$H NMR (200 MHz, CDCl$_3$): δ0.96 (t; 3 H), 1.1–1.7 (m; 8 H), 4.3–4.5 (m; 1 H), 8.20 (dd; 1 H), 8.85 (s; 1 H) ppm.

Melting point: 118°–121° C.

Example Z 8

Ethyl 1-cyclopropyl-6,7-difluoro-1,4-dihydro-8-(3,3-dimethylbutin- 1-yl)-4-oxo-3-quinolinecarboxylate Analogously to Example Z6, 1-tributylstannyl-3,3-dimethyl-but-1-ine gives 0.87 g of ethyl 1-cyclopropyl-6,7-difluoro- 1,4-dihydro-8-(3,3-dimethylbutin-1-yl)-4-oxo-3-quinolinecarboxylate (46% of theory).

Melting point: 170°–172° C.

Example Z 9

1-Cyclopropyl-6,7-difluoro-1,4-dihydro-8-(3,3-dimethylbutin- 1-yl)-4-oxo-3-quinolinecarboxylic acid Hydrolysis of 0.75 g of the ester from Example Z8 analogously to Example Z7 gives 0.56 g of 1-cyclopropyl-6,7-difluoro- 8-(3,3-dimethylbutin-1-yl)-4-oxo-3-quinolinecarboxylic acid (81% of theory).

Melting point: 199°–201° C.

Example Z10

Ethyl 1-(2,4-difluorophenyl)-6,7-difluoro-1,4-dihydro-8-(trimethylsilylethinyl)- 4-oxo-3-quinolinecarboxylate 6.7 g of ethyl 8-bromo-1-(2,4-difluorophenyl)-6,7-difluoro- 1,4-dihydro-4-oxo-3-quinolinecarboxylate (Example Z20), 10.8 g of tributylstannyl-trimethylsilyl-acetylene and 0.87 g of tetrakis(triphenylphosphine)-palladium(0) are refluxed for 24 hours in 50 ml of absolute toluene under a nitrogen atmosphere. The product crystallises from the reaction mixture at −18° C. 4.8 g of ethyl 1-( 2,4-difluorophenyl)-6,7-difluoro-1,4-dihydro-8-(trimethylsilylethinyl)-4-oxo-3-quinolinecarboxylate are obtained (69% of theory).

Melting point: 173°–174° C.

Example Z11

Ethyl 1-(2,4-difluorophenyl)-8-ethinyl-6,7-difluoro-1,4-dihydro- 4-oxo-3-quinolinecarboxylate A solution of 4.6 g of ethyl 1-(2,4-difluorophenyl)-6,7-difluoro- 1,4-dihydro-8-(trimethylsilylethinyl)-4-oxo-3-quinolinecarboxylate in 20 ml of chloroform is added dropwise at room temperature to a solution of 2 g of potassium fluoride in a solvent mixture of 3 ml of water, 25 ml of chloroform and 50 ml of dimethylformamide. The mixture is stirred for 1 hour at approx. 20° C., the reaction mixture is then treated with more chloroform and extracted several times by shaking with water, and the organic phase is dried and concentrated. The residue obtained is recrystallised from methanol. 3.4 g of ethyl 1-(2,4-difluorophenyl)-8-ethinyl-6,7-difluoro-1,4-dihydro- 4-oxo-3-quinolinecarboxylate are obtained (87% of theory).

Melting point: 189° C.

Example Z12

1-(2,4-Difluorophenyl)-8-ethinyl-6,7-difluoro-1,4-dihydro- 4-oxo-3-quinolinecarboxylic acid 1.17 g of ethyl 1-(2,4-difluorophenyl)-8-ethinyl-6,7-difluoro- 1,4-dihydro-4-oxo-3-quinolinecarboxylate are refluxed for 1 hour in a mixture of 9 ml of glacial acetic acid, 0.75 ml of water and 0.2 ml of concentrated sulphuric acid. The solid which has crystallised out at room temperature is filtered off with suction and dried. 0.98 g of 1-(2,4-difluorophenyl)-8-ethinyl-6,7-difluoro- 1,4-dihydro-4-oxo-3-quinolinecarboxylic acid is obtained (90% of theory).

Melting point: 220° C. (decomposition).

Example Z13

Ethyl 1-cyclopropyl-6,7-difluoro-1,4-dihydro-4-oxo-8-(propin- 1-yl)-3-quinolinecarboxylate 7.5 g of ethyl 8-bromo-1-cyclopropyl-6,7-difluoro-1,4-dihydro- 4-oxo-3-quinolinecarboxylate, 9.1 g of 1-tributylstannyl-prop-1-ine and 1.16 g of tetrakis(triphenylphosphine)palladium( 0) are refluxed for 8 hours in 80 ml of absolute toluene under a nitrogen atmosphere. The solid which crystallises out at −18° C. is filtered off with suction and dried. 2.05 g of ethyl 1-cyclopropyl- 6,7-difluoro-1,4-dihydro-4-oxo-8-(propin-1-yl)-3-quinolinecarboxylate are obtained (31% of theory).

$^1$H NMR (200 MHz, CDCl$_3$): δ1.1–1.35 (m; 4 H), 1.40 (t; 3 H), 2.16 (d; 3 H), 4.1–4.3 (m; 1H), 4.35 ( q; 2 H), 8.15 (dd; 1 H), 8.56 (s; 1 H) ppm.

Melting point: 180°–182° C.

Example Z14

1-Cyclopropyl-6,7-difluoro-1,4-dihydro-4-oxo-8-(propin-1-yl)- 3-quinolinecarboxylic acid 1.4 g of ethyl 1-cyclopropyl-6,7-difluoro-1,4-dihydro-4-oxo- 8-(propin-1-yl)-3-quinolinecarboxylate are refluxed for 1 hour in a mixture of 20 ml of glacial acetic acid, 1.5 ml of water and 0.5 ml of concentrated sulphuric acid. The mixture is treated with approx. 10 ml of water, and the solid which has precipitated is then isolated and dried. In this manner, 1.05 g of 1-cyclopropyl-6,7-difluoro- 1,4-dihydro-4-oxo-8-(propin-1-yl)-3-quinolinecarboxylic acid are obtained (82% of theory).

$^1$H NMR (200 MHz, CDCl$_3$): δ1.4 (m; 4 H), 2.26 (d; 3 H), 4.4–4.6 (m; 1 H), 8.16 (dd; 1 H), 8.81 (s; 1 H) ppm.

Melting point: 212°–213° C.

Example Z 15

Ethyl 1-ethyl-6,7-difluoro-1,4-dihydro-8-(trimethylsilyl-ethinyl)- 4-oxo-3-quinolinecarboxylate

5.4 g of ethyl 8-bromo-1-ethyl-6,7-difluoro-1,4-dihydro-4-oxo-3-quinolinecarboxylate (Example Z22), 10.8 g of tributylstannyl-trimethylsilyl-acetylene and 0.87 g of tetrakis(triphenylphosphine)palladium(0) are refluxed for 24 hours in 50 ml of absolute toluene under a nitrogen atmosphere. The reaction mixture is concentrated, the residue is stirred with 100 ml of hexane, and the resulting solid is filtered off with suction and dried. 4.53 g of ethyl 1-ethyl-6,7-difluoro-1,4-dihydro-8-(trimethylsilylethinyl)- 4-oxo-3-quinolinecarboxylate are obtained (80% of theory).

Melting point: 151°–152° C.

Example Z16

Ethyl 1-cyclopropyl-6,7-difluoro-1,4-dihydro-8-(trimethyl-silylethinyl)- 4-oxo-3-quinolinecarboxylate

1.64 g of ethyl 8-chloro-1-cyclopropyl-6,7-difluoro-1,4-dihydro- 4-oxo-3-quinolinecarboxylate, 3 g of tributylstannyl-trimethylsilyl-acetylene and 0.29 g of tetrakis(triphenylphosphine)palladium( 0) are refluxed for 42 hours in 20 ml of absolute toluene under a nitrogen atmosphere. The reaction mixture is cooled to approx. −18° C. and filtered. After the filter residue has been dried, 0.74 g of ethyl 1-cyclopropyl-6,7-difluoro-1,4-dihydro- 8-(trimethylsilylethinyl)-4-oxo-3-quinolinecarboxylate is obtained (38% of theory).

Example Z17

Ethyl 1-cyclopropyl-6,7-difluoro-1,4-dihydro-8-(3-methylbut-3-en-1-inyl)-4-oxo-3-quinolinecarboxylate

1.86 g of ethyl 8-bromo-1-cyclopropyl-6,7-difluoro-1,4-dihydro- 4-oxo-3-quinolinecarboxylate, 2.8 g of 1-tributylstannyl- 3-methyl-but-3-en-1-ine and 0.29 g of tetrakis(triphenylphosphine)palladium(0) are refluxed for 6 hours in 20 ml of absolute toluene under a nitrogen atmosphere. The reaction mixture is filtered under hot conditions and concentrated, and the residue is stirred with hexane. After filtration with suction and drying, 1.43 g of ethyl 1-cyclopropyl-6,7-difluoro-1,4-dihydro-8-( 3-methyl-but-3-en-1-inyl)-4-oxo-3-quinolinecarboxylate are obtained (80% of theory).

Melting point: 169°–171° C.

Example Z18

1-Cyclopropyl-6,7-difluoro-1,4-dihydro-8-(3-methyl-but-3-en- 1-inyl)-4-oxo-3-quinolinecarboxylic acid

0.715 g of ethyl 1-cyclopropyl-6,7-difluoro-1,4-dihydro-8-(3-methyl-but-3-en-1-inyl)-4-oxo-3-quinolinecarboxylate is refluxed for 1.5 hours in a mixture of 10 ml of glacial acetic acid, 0.5 ml of water and 0.2 ml of concentrated sulphuric acid. The reaction mixture is poured into 100 ml of water. The solid which has precipitated is filtered off with suction, washed with water and dried. 0.53 g of 1-cyclopropyl-6,7-difluoro-1,4-dihydro- 8-(3-methyl-but-3-en-1-inyl)- 4-oxo-3-quinolinecarboxylic acid is obtained (80% of theory).

Melting point: 204°–206° C.

Example Z19

Ethyl 2-(3-bromo-2,4,5-trifluoro-benzoyl)-3-(2,4-difluoro-phenylamino)-acrylate

40 g (0.1 mol) of ethyl 2-(3-bromo-2,4,5-trifluorobenzoyl)- 3-ethoxy-acrylate in 180 ml of ethanol are treated with 14.5 g (0.11 mol) of 2,4-difluoro-aniline, with ice-cooling. The mixture is allowed to stand overnight at 10° C., and the precipitated solid is filtered off with suction, washed with cold ethanol and dried in vacuo.

Yield: 38 g (81% of theory).

Melting point: 102°–103° C. (with decomposition) (from isopropanol).

Example Z20

Ethyl 8-bromo-1-(2,4-difluorophenyl)-6,7-difluoro-1,4-dihydro-4-oxo-3-quinolinecarboxylate

38 g (82 mmol) of ethyl 2-(3-bromo-2,4,5-trifluorobenzoyl)- 3-(2,4-difluorophenylamino)-acrylate in 200 ml of dimethylformamide are treated with 7.6 g of sodium fluoride and the mixture is refluxed for 2 hours. The mixture is poured into ice-water, and the precipitate is filtered off with suction, washed thoroughly with water and dried at 80° C. in a recirculation drying cabinet.

Yield: 34.7 g (95% of theory).

Melting point: 208°–210° C. (with decomposition) (from glycol monomethyl ether). Acid hydrolysis of this ester gives 8-bromo-1-(2,4-difluorophenyl)- 6,7-difluoro-1,4-dihydro-4-oxo-3-quinolinecarboxylic acid of melting point 210°–221° C. (with decomposition).

Example Z21

Ethyl 2-(3-bromo-2,4,5-trifluoro-benzoyl)-3-ethylaminoacrylate

20 g (0.05 mol) of ethyl 2-(3-bromo-2,4,5-trifluorobenzoyl)- 3-ethoxy-acrylate in 40 ml of ethanol are treated with 5.5 g of a 50% strength aqueous ethylamine solution, with ice-cooling. The mixture is allowed to stand overnight at 10° C., the suspension is treated with 200 ml of water, and the precipitated solid is filtered off with suction, washed with water and dried in vacuo at 60 ° C.

Yield: 17.3 g ( 91% of theory).

Melting point: 101°–102° C. (with decomposition) (from isopropanol).

Example Z22

Ethyl 8-bromo-1-ethyl-6,7-difluoro-1,4-dihydro-4-oxo-3-quinolinecarboxylate

16 g (42 mmol) of ethyl 2-(3-bromo-2,4,5-trifluorobenzoyl)- 3-ethylaminoacrylate are reacted analogously to Example Z20.

Yield: 14.6 g (96% of theory).

Melting point: 172°–173° C. (with decomposition) (from glycol monomethyl ether). Acid hydrolysis of this ester gives 8-bromo-1-ethyl-6,7-difluoro- 1,4-dihydro-4-oxo-3-quinolinecarboxylic acid of melting point 215°–217° C. (with decomposition).

Example Z23

4-Methylamino-1,3,3a,4,7,7a-hexahydroisoindole

Method I:

10.1 g (60 mmol) of N-trimethylsilylmaleimide [J.Org. Chem. 40, 24 (1975)] in 30 ml of absolute tetrahydrofuran are introduced into a reaction vessel, and 14.4 g (60 mmol) of 70% 1-(tert.-butyloxycarbonylamino)-1,3-butadiene [J.Org.Chem. 43, 2164 (1978)], dissolved in 30 ml of absolute tetrahydrofuran, are added dropwise. When the exothermic reaction has subsided, the mixture is refluxed for a further hour.

7.6 g (0.2 mol) of lithium aluminium hydride in 200 ml of absolute tetrahydrofuran are introduced into a reaction vessel, and the cold reaction mixture is then added dropwise under nitrogen. The mixture is then refluxed for 14 hours. 7.6 g of water in 23 ml of tetrahydrofuran, 7.6 g of 10% strength sodium hydroxide solution and 22.8 g of water are then added dropwise in succession to the cold reaction mixture. The salts are filtered off and the filtrate is concentrated in vacuo. The residue (10.3 g) is distilled at 87° C./0.8 mbar.

The distillate is taken up in 80 ml of absolute pentane, the mixture is filtered, and the product is crystallised by cooling the filtrate to −70° C.

Yield: 3.3 g, melting point: 72°–82° C.

Treatment with an equimolar amount of 2N hydrochloric acid gives 4-methylamino-1,3,3a,4,7,7a-hexahydro-isoindole dihydrochloride of melting point 265°–268° C. (from methanol).

Method II:

a) 4-(tert.-Butyloxycarbonylamino)-1,3-dioxo- 1,3,3a,4,7,7a-hexahydroisoindole 48.0 g (0.5 mol) of maleimide dissolved in 200 ml of absolute tetrahydrofuran are introduced into a reaction vessel, and 120 g (0.5 mol) of approx. 70% 1-(tert.-butyloxycarbonylamino)-1,3-butadiene dissolved in 500 ml of absolute tetrahydrofuran are added dropwise, during which process the temperature is kept at 20° to 30° C. Stirring is continued overnight at room temperature. The mixture is then concentrated, and the product is recrystallised from ethyl acetate. 57 g of product of a melting point of 177° to 182° C. are obtained. A further 13 g of a melting point of 158° to 160° C. are obtained from the mother liquor.

b) 4-Methylamino-1,3,3a,4,7,7a-hexahydroisoindole

Under nitrogen, 27.1 g (0.71 mol) of lithium aluminium hydride are introduced into 300 ml of absolute tetrahydrofuran, and a solution of 57 g (0.21 mol) of 4-(tert.-butyloxycarbonylamino)-1,3-dioxo- 1,3,3a,4,7,7a-hexahydroisoindole in 570 ml of absolute tetrahydrofuran is added dropwise. The mixture is then refluxed overnight. 27.1 g of water in 82 ml of tetrahydrofuran, 27.1 g of 10% strength sodium hydroxide solution and 81.3 g of water are then added dropwise to the cold batch. The salts are filtered off with suction and washed with tetrahydrofuran, and the filtrate is concentrated in vacuo. The residue is distilled off under a high vacuum.

Yield: 19.1 g.

Example Z24

4-Amino-1,3,3a,4,7,7a-hexahydro-isoindole 13.3 g (50 mmol) of 4-tert.-butyloxycarbonylamino-1,3-dioxo- 1,3,3a,4,7,7a-hexahydro-isoindole (from Example Z23, method II) are stirred overnight at room temperature in 166 ml of trifluoroacetic acid. The trifluoroacetic acid is then distilled off at 10 mbar, and the residue is freed from remaining acid in a high vacuum at 50° C. The residue is subsequently taken up in absolute tetrahydrofuran and concentrated in vacuo. The residue is taken up in 100 ml of absolute tetrahydrofuran and the mixture is added dropwise under nitrogen to a solution of 11.3 g (0.3 mol) of lithium aluminium hydride in 300 ml of absolute tetrahydrofuran. The mixture is then refluxed for 16 hours. 11.3 g of water in 34 ml of tetrahydrofuran, 11.3 ml of 10% strength sodium hydroxide solution and 34 ml of water are added dropwise in succession to the cold mixture. The precipitate is filtered off with suction and washed with tetrahydrofuran. The filtrate is concentrated, and the residue is distilled.

Yield: 2.2 g, content: 92% (determination by gas chromatography)

Boiling point: 70° C./0.2 mbar.

Example Z25

7-Methyl-4-methylamino-1,3,3a,4,7,7a-hexahydro-isoindole

Analogously to Example Z23, method I, 21.9 g (0.12 mol) of 1-(tert.-butyloxycarbonylamino)-1,3-pentadiene are reacted with 20.3 g (0.12 mol) of N-trimethylsilylmaleimide, and the product is subsequently reduced with 15.2 g (0.4 mol) of lithium aluminium hydride. The crude product is recrystallised from tetrahydrofuran.

Yield: 6.2 g, melting point: 106°–108° C.

Example Z26

1-Cyclopropyl-6,7-difluoro-1,4-dihydro-8-(3-methoxypropin- 1-yl)-4-oxo-3-quinolinecarboxylic acid A) 1.86 g (5 mmol) of ethyl 8-bromo-1-cyclopropyl-6,7-difluoro- 1,4-dihydro-4-oxo-3-quinolinecarboxylate in 20 ml of absolute toluene are treated with 2.5 g (7 mmol) of 1-tributyl-stannyl-3-methoxy-propine and 0.29 g (corresponding to 5 mol %) of tetrakis(triphenylphosphine)-palladium(0), and the mixture is refluxed for 4 hours in a nitrogen atmosphere. The reaction mixture is concentrated, the residue is stirred with hexane, and the solid is filtered off with suction and purified by chromatography over a little silica gel.

Yield: 0.74 g ( 41% of theory) of ethyl 1-cyclopropyl-6,7-difluoro-1,4-dihydro-8-(3-methoxy-propin- 1-yl)-4-oxo-3-quinolinecarboxylate.

Melting point: 144°–146° C.

B) 0.36 g (1 mmol) of the product of stage A is refluxed for 1 hour in a mixture of 3 ml of glacial acetic acid, 0.2 ml of water and 0.05 ml of concentrated sulphuric acid. The mixture is poured into water, and the precipitate is filtered off and recrystallised from ethanol.

Yield: 153 mg (46% of theory) of 1-cyclopropyl-6,7-difluoro- 1,4-dihydro-8-(3-methoxy-propin-1-yl)-4-oxo-3-quinolinecarboxylic acid.

Melting point: 170°–172° C.
¹H NMR (270 MHz, CDCl₃): δ1.24 m (2H), 1.4 m (2H), 3.45 s (OCH₃), 4.35 m (1H), 4.41 s (O—CH₂—), 8.27 "t" (1H), 8.87 ppm s (1H).

Example Z27

[S,S]-2,8-diazabicyclo[4.3.0]nonane

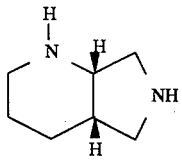

1) [S,S]-8-benzyl-2,8-diazabicyclo[4.3.0]nonane

Method I:

a) Separating the diastereomeric salts 3.0 g (20 mmol) of D(–)-tartaric acid are dissolved by heating to 80° C. in 10 ml of dimethylformamide and treated with a solution of 2.16 g (10 mmol) of cis-8-benzyl-2,8-diazabicyclo[ 4.3.0]nonane in 3 ml of dimethylformamide. The batch is agitated for 1 hour at 0° C., suctioned off, and washed with dimethylformamide and methoxyethanol.

Yield: 1.93 g

Melting point: 146°–151° C. $[\alpha]_D^{23}$=–19.3° C. (c=1, H₂O).

Diastereomerically pure [S.S]-8-benzyl-2,8-diazabicyclo[ 4.3.0]nonane D-tartrate is obtained by recrystallizing from methoxyethanol.

$[\alpha]_D^{23}$=–22.7° C. (c=1, H₂O).

Melting point: 148°–154° C.

b) Liberation of the base 40 g of [S,S]-8-benzyl-2,8-diazabicyclo[4.3.0]nonane D-tartrate are dissolved in 250 ml of water and treated with 32 g of 45% sodium-hydroxide solution. The resulting oil is taken up in 150 ml of tert.-butylmethylether. The aqueous phase is extracted again with 150 ml of tert.-butylmethyl-ether.

The combined organic phases are dried over sodium sulfate and concentrated. Distillation proceeds in a vacuum.

Yield: 18.5 g of [S,S]-8-benzyl-2,8-diazabicyclo[4.3.0] nonane

Boiling point: 107°–109° C./0.1 mbar.

$[\alpha]_D^{24}$=17.3° C. (undiluted).

Method II:

75.0 g (0.5 mol) of L(+)-tartaric acid are dissolved in 250 ml of dimethylformamide at 80° C., and 54.1 g (0.25 mol) of cis-8-benzyl-2,8-diazabicyclo[4.3.0]nonane dissolved in 75 ml of dimethylformamide added dropwise. The batch is gradually cooled to 20° C. and the crystal suspension agitated for 1 hour. The crystals, [R,R]-8-benzyl- 2,8-diazabicyclo-[4.3.0]nonane L-tartrate, are suctioned off and the filtrate concentrated in a rotary evaporator. The residue is dissolved in 500 ml of water and processed with 63 g of a 45% sodium-hydroxide solution as described for Method I.

Yield: 25.2 g of [S,S]-8-benzyl-2,8-diazabicyclo[4.3.0] nonane, the product containing 3.6% of the R,R-enantiomer (as determined by gas chromatography subsequent to derivatization with menthyl chloroformate).

The compound can be converted by Method I with D(–)-tartaric acid into diastereomerically pure [S,S]-8-benzyl- 2,8-diazabicyclo[4.3.0]nonane D-tartrate. Recrystallizing is unnecessary in this case.

Method III 73.6 g (0.34 mol) of cis-8-benzyl-2,8-diazabicyclo[ 4.3.0] nonane dissolved in 111 ml of dimethylformamide is added a drop at a time to a solution of 102.9 g (0.685 mol) of L(+)-tartaric acid in 343 ml of dimethylformamide. The batch is seeded with [R,R]-8-benzyl-2,8-diazabicyclo[ 4.3.0]nonane L-tartrate and gradually cooled to an interior temperature of 18° C. The crystals are suctioned off and the filtrate seeded with [S,S]-8-benzyl-2,8-diazabicyclo[ 4.3.0] -nonane L-tartrate and agitated until it crystallizes completely. ([S,S]-8-benzyl-2,8-diazabicyclo[ 4.3.0]nonane D-tartrate can be obtained from the mother liquor subsequent to concentration and release of the base by purification with D(–)-tartaric acid as described for Method I.) The product is suctioned off, washed with dimethylformamide and isopropyl alcohol, and dried in the air. The crystals are recrystallized from 88% ethanol. 52 g of [S,S]-8-benzyl-2, 8-diazabicyclo[4.3-O]nonane L-tartrate trihydrate are obtained.

Melting point: 201°–204° C.

$[\alpha]_D^{23}$=+5.2° C. (c=1, H₂O).

The salt can be processed as described for Method I (releasing the base) into enantiomerically pure [S,S]-8-benzyl-2,8-diazabicyclo-[4.3.0]nonane.

Method IV:

a) Enantiomeric separation of cis-8-benzyl-7,9-dioxo-2, 8-diazabicyclo[ 4.3.0]nonane into [1S,6R]-8-benzyl-7, 9-dioxo- 2,8-diazabicyclo[4.3.0]nonane One approach is similar to the procedure described in Example Z28 (Method II/a), with D(–)-tartaric acid as a chiral auxiliary reagent. Another procedure is also possible and will now be described.

The mother liquor and the washing liquor from the [1R,6S]-8-benzyl-7,9-dioxo-2,8-diazabicyclo[4.3.0]nonane L-tartrate (Example Z28, Method II/a) are concentrated together, taken up in water, and extracted three times with toluene. The toluene phases are discarded. The aqueous phase is treated with a saturated sodium hydrogen-carbonate solution until the Ph is 7 to 8 and extracted four times with methylene chloride. The combined methylene chloride phases are dried over magnesium sulfate and concentrated.

Yield: 14.4 g (60% of the theoretical from the originally employed racemic cis-8-benzyl-7,9-dioxo-2,8-diazabicyclo[ 4.3.0]nonane).

$[\alpha]_D^{23}$=–4.5° (c=5, ethanol).

These 14.4 g (59 mmol) are crystallized with 8.6 g (57 mmol) of D(–)-tartaric acid as described for Example Z28 Method II/a).

Yield: 8.9 g (77% of the theoretical) of [1S,6R]-8-benzyl-7,9-dioxo-2,8-diazabicyclo-[4.3.0]nonane D-tartrate.

$[\alpha]_D^{23}$=–46.2° (c=0.5, 1 n HCl).

$[\alpha]_D^{23}$ subsequent to recrystallization from a mixture of ethanol and ethylene-glycol monomethylether and further purification: –59.3° (c=0.5, 1 n HCl).

5.0 g (12.7 mmol) of the accordingly obtained diastereomerically pure tartrate were transformed as described in Example Z28, Method II/a into the free amine.

Yield: 3.0 g (96% of the theoretical) of [1S,6R]-8-benzyl-7,9-dioxo-2,8-diazabicyclo[4.3.0]nonane.

Melting point: 60°–61° C.

$[\alpha]_D^{23}=-22.2°$ (c=5, ethanol).

An enantiomeric excess of 96.6% was determined by gas chromatography subsequent to derivatization with menthyl chloroformate.

b) Reduction of [1S,6R]-8-benzyl-7,9-dioxo-2,8-diazabicyclo[ 4.3.0]nonane to [S,S]-8-benzyl-2,8-diazabicyclo [4.3.0]nonane The procedure is analogous to that described for Example Z28 (Method II, b), but with [1S,6R]-8-benzyl-7,9-dioxo-2,8-diazabicyclo[4.3.0]nonane as the educt.

The crude product of the process turned out during derivatization with menthyl chloroformate to be [S,S]-8-benzyl-2,8-diazabicyclo[4.3.0]-nonane. No racemization was observed during reduction.

2) [S,S]-2,8-diazabicyclo[4.3.0]nonane 28.4 g (0.131 mol) of [S,S]-8-benzyl-2,8-diazabicyclo[ 4.3.0]nonane are hydrogenated for up to 5 hours in 190 ml of methanol over 5.8 g of palladium on active carbon (5%) at 90° C. and 90 bar. The catalyst is suctioned off and washed with methanol and the filtrate is concentrated in a rotary evaporator. The residue is distilled without fractionation.

Yield: 15.0 g (90.5% of the theoretical) of [S,S]-2,8-diazabicyclo[ 4.3.0]nonane.

$[\alpha]_D^{22}=-2.29°$ (undiluted).

ee>99% (determined by gas chromatography subsequent to derivatization with Mosher's reagent).

Method V:

3.75 g (25 mmol) of L-(+)-tartaric acid are dissolved in 50 ml of dimethylformamide at 80° C. and 10.82 g (50 mmol) of cis-8-benzyl-2,8-diazabicyclo[4.3.0]nonane dissolved in 15 ml of dimethylformamide added dropwise. The batch is seeded with [R,R]-S-benzyl-2,8-diazabicyclo[4.3.0]nonane L-tartrate and agitated one hour at approximately 72° C. until the seed is completely established. The bath is cooled gradually to 15° C., the crystals are suctioned off, and washed twice with 13 ml of dimethylformamide. The combined filtrates are heated to 80° C. and treated with another 3.75 g (25 mmol) of L-(+)-tartaric acid. The batch is heated again to 119° C. until the solution clears and cooled gradually back to room temperature while being seeded with [S,S]-8-benzyl-2,8-diazabicyclo[4.3.0]nonane L-tartrate. The crystals are suctioned off washed with dimethylformamide, with 2-methoxyethanol, and with ethanol, and dried in the air.

Yield: 9.59 g.

Melting point: 188° to 192° C.

The crystals are recrystallized from 95 ml of 80% ethanol. 8.00 g of [S,S]-8-benzyl-2,8- diazabicyclo[4.3.0]nonane L-tartrate trihydrate (76% of theoretical) are obtained. It melts with foaming at 112° to 118° C., solidifies again, and melts again at 199° to 201° C.

$[\alpha]_D^{23}=4.5°$ (C=1, water)

ee: 98.0% (determined by gas chromatography subsequent to derivatization with menthyl chloroformate).

Example Z28

[R,R]-2,8-diazabicyclo[4.3.0]nonane

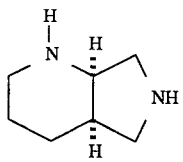

1) [R,R]-8-benzyl-2,8-diazabicyclo[4.3.0]nonane

Method I

The crystals of[R,R]-8-benzyl-2,8-diazabicyclo[4.3.0] nonane obtained by Example Z27, Method II are washed with dimethylformamide and methoxyethanol (49.2 g) and recrystallized from 300 ml of methoxyethanol. 45.6 g of enantiomerically pure [R,R]-8-benzyl-2,8-diazabicyclo[ 4.3.0]nonane L-tartrate are obtained (the enantiomeric purity determined by gas chromatography subsequent to derivatization with menthyl chloroformate).

Melting point: 121°–124° C.

$[\alpha]_D^{23}=+22.3°$ (C=1, H$_2$O).

The salt (44.5 g) is converted into the free base as described in Example Z27, Method Ib.

20.2 g of [R,R]-8-benzyl-2,8-diazabicyclo[4.3.0]nonane are obtained.

Boiling point: 107°–111° C. at 0.04 mbar. $[\alpha]_D^{24}=-17.5°$ (undiluted).

Method II a) Enantiomeric separation of cis-8-benzyl-7,9-dioxo-2,8-diazabicyclo[4.3.0]nonane to give [1R,6S]-8-benzyl- 7,9-dioxo-2,8-diazabicyclo[4.3.0]nonane 24.1 g (98.8 mmol) of cis-8-benzyl-7,9-dioxo-2,8-diazabicyclo[ 4.3.0]-nonane are heated to reflux with stirring in a mixture of 410 ml of ethanol and 25 ml of acetonitrile in a three-necked flask. 14.8 g (98.8 mmol) of L-(+)-tartaric acid are added all at once. Once all the acid has completely dissolved, the heating is discontinued although the flask is left standing in the oil bath. Once the system has cooled down until the solution stops boiling, the agitator is turned off. Crystallization occurs at 50° C. subsequent to the addition of seed crystals. The batch is left to cool to room temperature overnight. The precipitated crystals are suctioned off, washed with a little ethanol and petroleum ether (1:1), and dried 2 hours at 80° C.

Yield: 9,8 g (50% of the theoretical) of [1R, 6S]-8-benzyl-7,9-dioxo-2,8-diazabicyclo-[4.3.0]nonane L-tartrate. $[\alpha]_D^{23}=+47.7°$ (c=0.5, 1 n HCl).

Two recrystallizations from a mixture of ethanol and ethylene-glycol monomethyl ether purifies the compound even further.

$[\alpha]_D^{23}=+58.6°$ (c=0.5, 1 n HCl).

$^1$-NMR (DMSO): 7.22–7.35 (2m, 2H, aryl-H); 4.55 (s, 2H, benzyl-CH$_2$); 4.28 (s, 2H, tartaric acid-CH); 3.91 (d, 1H, 1-CH); 2.97 (dd, 1H, 6-CH); 2.53–2.66 (m, 2H, 3-CH$_2$); 1.78 and 1.68 (2m, 2t, 5-CH$_2$); 1.42 and 1.28 ppm (2m. 2H, 4-CH$_2$).

C$_{18}$H$_{22}$N$_2$O$_8$ (394) Calculated: C 54.4 H 5.6 N 7.1 O 32.5 Found: C54.7 H 5.8 N 7.1 O 32.4

The absolute structure, obtained by X-ray analysis, was

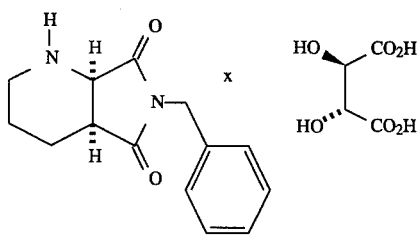

3.6 g (9.1 mmol) of the accordingly obtained diastereomerically pure tartrate is dissolved in water to release the base and treated with saturated sodium hydrogen-carbonate solution until the Ph is 7 to 8. The aqueous solution is extracted four times with 20 ml of methylene chloride each. The purified methylene-chloride phases are dried over magnesium sulfate and concentrated.

Yield: 2.2 g (99% of the theoretical) of [1R,6S]-8-benzyl-7,9-dioxo-2,8-diazabicyclo[4.3.0]nonane. Melting point: 60°–61° C. $[\alpha]_D^{23}=+21.8°$ (c=5 ethanol).

An enantiomeric excess of 93.8% was determined subsequent to derivatization with menthyl chloroformate.

b) Reduction of [1R,6S]-8-benzyl-7,9-dioxo-2,8-diazabicyclo[4.3.0]nonane to [R,R]-8-benzyl-2,8-diazabicyclo[4.3.0]nonane 0.34 g (9 mmol) of lithium aluminum hydride in 18 ml of anhydrous tetrahydrofuran are added under $N_2$ to a heat-dried flask. 0.73 g (3 mol) of [1R,6S]-8-benzyl-7,9-dioxo-8-diazabicyclo[4.3.0]nonane dissolved in 3 ml of anhydrous tetrahydrofuran are added dropwise. The batch is boiled and reflux cooled for 16 hours. Processing occurs by adding 0.34 ml of water in 10 ml of tetrahydrofuran, 0.34 ml of 10% sodium-hydroxide solution, and 1.02 ml of water drop by drop. The precipitate is suctioned off and washed with tetrahydrofuran and the filtrate is concentrated, leaving 0.7 g of crude [R,R]-8-benzyl-2,8-diazabicyclo[4.3.0]nonane (gas chromatography indicating a 99% content). Gas chromatography of the enantiomeric purity with menthyl chloroformate indicated no racemization.

2) [R,R]-2,8-diazabicyclo[4.3.0]nonane 19.4 g (0.09 moles) of [R,R]-8-benzyl-2,8-diazabicyclo[4.3.0]nonane are hydrogenated as described in Example Z27, 2.

Yield: 9.61 g (85%) of [R,R]-2,8-diazabicyclo[4.3.0]nonane.

Boiling point: 45°–58° C. at 0.08 mbar. $[\alpha]_D^{23}=+2.30°$ (undiluted)

Example Z29 cis-2-oxa-5,8-diazabicyclo[4.3.0]nonane

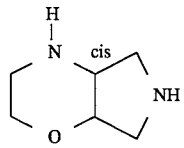

1) Trans-1-benzoyl-3-bromo-4-(2-hydroxyethoxy)-pyrrolidine 95 g (0.55 mol) of 1-benzoyl-3-pyrrolidine are dissolved in 380 g of ethylene glycol. 101 g (0.57 mol) of N-bromosuccinimide are added 5 g at a time at room temperature over an interval of 2 hours. The batch is agitated overnight at room temperature, poured into water, extracted with methylene chloride, dried over magnesium sulfate, and concentrated. The residue (188 g) was chromatographed with ethyl acetate on silica gel.

Yield: 136.5 g (78% of theoretical) Content by gas chromatography: 99%.

2) Trans-1-benzoyl-3-bromo-4-(2-tosyloxyethoxy)-pyrrolidine 92 g (0,239 mol) of trans-1-benzoyl-3-bromo-4-(2-hydroxyethoxy)-pyrrolidine, 32 g (0.316 mol) of triethylamine, and 1 g of 4-dimethylaminopyridine are dissolved in 750 ml of toluene. 60 g (0.31 mol) of tosyl chloride in 450 ml of toluene are added dropwise. The batch is stirred two days at room temperature, water is added, and the aqueous phase separated and extracted with toluene. The toluene solutions are washed with 10% hydrochloric acid, dried over magnesium sulfate, concentrated, dissolved in ethyl acetate, and filtered through silica gel. The filtrate is concentrated.

Yield: 125 g (91% of theoretical).

Thin-layer chromatography reveals a uniform compound.

3) Cis-8-benzoyl-5-benzyl-2-oxa-5,8-diazabicyclo[4.3.0]-nonane 124 g (0.265 mol) of trans-1-benzoyl-3-bromo-4-(2-tosyloxyethoxy)-pyrrolidine are re-fluxed overnight with 86 g (0.8 mol) of benzylamine in 1.5 l of xylene. The benzylamine salts are suctioned off and the filtrate concentrated.

Raw yield: 91.2 g.

4) Cis-5-benzyl-2-oxa-5,8-diazabicyclo[4.3.0]nonane 91 g (0.265 mol) of cis-8-benzoyl-5-benzyl-2-oxa-5,8-diazabicyclo[4.3.0]nonane are refluxed overnight with 200 ml of concentrated hydrochloric acid and 140 ml of water. The batch is cooled and the benzoic acid suctioned off. The batch is concentrated to half its original volume, adjusted to alkalinity with potassium carbonate, extracted with chloroform, dried over potassium carbonate, concentrated, and distilled.

Yield: 30.7 g (48.8% of theoretical). Boiling point: 134°–142° C. at 0.6 mbar. Content by gas chromatography: 92%.

5) Cis-2-oxa-5,8-diazabicyclo[4.3.0]nonane dihydrochloride 26 g (0.11 mol, 92%) of cis-5-benzyl-2-oxa-5,8-diazabicyclo-[4.3.0]nonane are hydrogenated in 180 ml of ethanol and 19 ml of concentrated hydrochloric acid over 3 g of palladium (10%) on active carbon at 100° C. and under 100 bar of $H_2$. The catalyst is suctioned off, the filtrate concentrated, and the precipitated crystals dried over phosphorus pentoxide in a desiccator.

Yield: 17.1 g (77% of theoretical) Melting point: 244°–250° C.

Example Z30

Enantiomeric separation of cis-5-benzyl-2-oxa-5,8-diazabicyclo[4.3.0]nonane 218.3 g (1 mol) of cis-5-benzyl-2-oxa-5,8-diazabicyclo-[4.3.0]nonane dissolved in 300 ml of methanol are added dropwise to 150.1 g (1 mol) of D(−)-tartaric acid in 700 ml of methanol at 60° to 65° C. The batch is allowed to cool down gradually to approximately 49° C., whereupon the solution becomes cloudy. The batch is seeded with previously obtained crystals of 1R,6S-5-benzyl-2-oxa-5,8-diazabicyclo[4.3.0]nonane D-tartrate, stirred 30 minutes at the same temperature to allow the seed crystals to form, and gradually cooled to 0° to 3° C. Suctioning is followed by washing first with a 0° C. mixture of 200 ml of ethanol and 100 ml of methanol and then three times with 300 ml of ethanol each. Finally, the product is dried in the air.

Yield: 160,3 g of 1R,6S-5-benzyl-2-oxa-5,8-diazabicyclo[ 4.3.0]nonane D-tartrate (87% of theoretical) Melting point: 174.5° to 176.5° C.

ee>97% (subsequent to derivatization with 1-phenylethyl isocyanate and high-pressure liquid chromatography) $[\alpha]_D^{23}$=24.0° (c=1, methanol)

156.9 g of the first crystallization are recrystallized from 1500 ml of methanol.

Yield: 140.0 g (89% recovered). Melting point: 176° to 177° C. $[\alpha]_D^{23}$=+25.2° (c=1, methanol).

The methanolic mother liquor from the first crystallization is concentrated in a rotary evaporator. The syrupy residue (236 g) is dissolved ion 500 ml of water, adjusted to a Ph of 12 to 13 with 250 ml of 6 n sodium-hydroxide solution, and extracted 3 times with 350 ml of toluene each. The extract is dried over sodium carbonate and concentrated in a vacuum. The residue, 113.1 g of brown oil, which gas chromatography reveals to contain 97% cis-5-benzyl-2-oxa-5,8-diaza-bicyclo[4.3.0]nonane, is employed without purification to prepare the 1S,6R enantiomer.

113.1 g (0.518 mol) of raw enriched 1S,6R-5-benzyl-2-oxa-5,8-diazabicyclo[4.3.0]nonane are dissolved in 155 ml of methanol and added dropwise to a boiling solution of 77.8 g (0.518 mol) of (+)-tartaric acid in 363 ml of methanol. A crystalline sludge begins to form gradually even while the solution is being added. The bath is agitated for an hour at 60° C. and gradually cooled to 0° C. over an interval of 2 hours. The crystals are suctioned off and washed first with a 0° C. 2:1 mixture of ethanol and methanol and then three times with ethanol alone. The product is dried in air.

Yield: 145 g of 1S,6R-5-benzyl-2-oxa-5,8-diazabicyclo[ 4.3.0]nonane L-tartrate (79% of theoretical). Melting point: 174.5° to 176.5° C.

ee>97% (subsequent to derivatization with 1-phenylethyl isocyanate and to high-pressure liquid chromatography).

$[\alpha]_D^{23}$=-24.0° (c=1, methanol)

Liberation of the enantiomerically pure bases 175 ml (1.05 mol) of 6 n sodium-hydroxide solution are added to 144 g (0.39 mol) of 1S,6R-5-benzyl-2-oxa-5,8-diazabicyclo[ 4.3.0]nonane tartrate are dissolved in 250 ml of water. The precipitated oil is taken up in 500 ml of toluene, the organic phase separated, and the aqueous phase extracted 3 more times with 250 ml of toluene each. The united organic phases are dried over sodium carbonate, filtered, and concentrated in a rotary evaporator. The residue is distilled in a 20 cm Vigreux column in a powerful vacuum.

Yield: 81.6 g (96% of the theoretical) of 1S,6R-5-benzyl-2-oxa-5,8-diazabicyclo[4.3.0]nonane Boiling point: 120° to 139° C. at 0.04 to 0.07 mbar. Content: 100% by gas chromatography. Density δ=1.113 g/ml. $[\alpha]_D^{23}$=-60.9° (undiluted). Distillation residue: 0.12 g.

76.0 g (93% of theoretical) of 1R,6S-5-benzyl-2-oxa-5,8diazabicyclo[ 4.3.0]nonane are similarly obtained from 139.2 g (0.376 mol) of 1R,6S-5-benzyl-2-oxa-5,8-diazabicyclo [4.3.0]nonane tartrate.

$[\alpha]_D^{23}$=+61.2° (undiluted).

The enantiomeric separation described in relation to the cis-5-benzyl-2-oxa-5,8-diazabicyclo [4.3.0]nonane can similarly be carried out with trans-5-benzyl-2-oxa-5,8-diazabicyclo[ 4.3.0] nonane, resulting in R,R- and S,S-5-benzyl-2-oxa-5,8-diazabicyclo[4.3.0]nonane.

Example Z31

1) tert.-butyl 3S,4S-4-allyloxy-3-hydroxypyrrolidine-1-carboxylate 107.5 g (0.53 mol) of tert.-butyl S,S-3,4-dihydroxypyrrolidine- 1-carboxylate (German OS 3 403 194) dissolved in hot absolute dioxane is added dropwise to 16.5 g (0.55 mol) of 80% sodium hydride in 500 ml of absolute dioxane at 60° C. The batch is stirred one hour at 60° C. 64 g (0.53 mol) of allyl bromide are added a drop at a time. The batch is agitated three hours at 60° C. It is concentrated and the residue dissolved in 200 ml of water and 600 ml of methanol. Extraction is carried out three times with 200 ml of pentane each, and the methanol is extracted in a rotary evaporator, diluted with 200 ml of water, and extracted with methylene chloride. The methylene chloride solution is dried over magnesium sulfate, concentrated, and dissolved in 200 ml of tert.-butylmethylether. 9 g (44 mmol) of educt crystallize out overnight. The ether solution is concentrated and distilled.

Yield: 83 g (80% of theoretical in terms of recovered educt and diallylether). Boiling point: 149° C. at 0.7 mbar to 159° C. at 0.9 mbar.

The distillate contains 5% of the educt and 4% of the diallylether.

The pentane extract supplied 17 g of a mixture of 15% of the desired product and 84% of the diallylether.

$[\alpha]_D^{23}$=-10.5° (c=1, methanol).

2) tert.-butyl 3S,1S-3-hydroxy-4-(2-hydroxyethoxy)-pyrrolidine- 1-carboxylate 64 g (0.24 mol, 91% strength) of tert.-butyl 3S,4S-4-allyloxy- 3-hydroxy-pyrrolidine-1-carboxylate are dissolved in 250 ml of methanol and cooled to 0° C. Ozone is bubbled through the solution until a washing bottle of potassium-iodide solution indicates the appearance of ozone and hence complete conversion. Residual ozone is extracted with flowing nitrogen and the ozonide reduced with 18 g of sodium borohydride, added 1 g at a time. The batch is agitated overnight at room temperature, concentrated, diluted with water, treated with 20 g of potassium carbonate, and extracted five times with 100 ml of methylene chloride each. The organic solutions are dried over magnesium sulfate and concentrated.

Yield: 65.8 g (100% of theoretical). Gas chromatography indicates a 91% product. $[\alpha]_D^{20}$=-15.2° (c=0.97, methanol)

3) 3S,4S-1-tert.- butoxycarbonyl-3-tosyloxy-4-(2-tosyloxyethoxy-pyrrolidine 6 ml of 45% sodium-hydroxide solution and 0.1 g of benzyltriethylammonium chloride are added to 2.7 g (10 mmol, 91% strength) of tert.-butyl 3S,4S-3-hydroxy-4-(2-hydroxy-ethoxy)-pyrrolidine-1-carboxylate in 30 ml of methylene chloride. A solution of 2.86 g (20 mmol) of tosyl chloride in 10 ml of methylene chloride are added a drop at a time to the batch while it is being kept cool. The batch is agitated an hour at room temperature and poured into 20 ml of water. The organic phase is separated and the aqueous phase extracted with methylene chloride. The organic phases are dried over magnesium sulfate and concentrated.

Yield: 5 g (90% of theoretical).

Thin-layer chromatography reveals a pure product.

4) tert.-Butyl 1S,6R-5-benzyl-2-oxa-5,8-diazabicyclo[ 4.3.0]nonane-8-carboxylate 87 g (156 mmol) of 3S,4S-1-tert.-butoxycarbonyl-3-tosyloxy- 4-(2-tosyloxyethoxy)-pyrrolidine are refluxed overnight with 58 g (0.54 mol) of benzylamine in 1 l of xylene. The batch is cooled, the precipitated benzylamine salts suctioned off, and the residue concentrated.

Yield: 43 g (58% of theoretical). Gas chromatography indicates a 67% product.

5) 1S,6R-5-Benzyl-2-oxa-5,8-diazabicyclo[4.3.0]nonane 43 g (90 mmol) of tert.-butyl 1S,6R-5-benzyl-2-oxa-5,8-diazabicyclo[4.3.0]nonane-S-carboxylate in 35 ml of concentrated hydrochloric acid and 35 ml of water are refluxed until no more carbon dioxide occurs. The mixture is adjusted alkaline with potassium carbonate and extracted with chloroform. The organic solutions are dried over magnesium sulfate, concentrated, and distilled twice in a 20 cm Vigreux column.

Yield: 11.1 g (55% of theoretical). Boiling point: 108°–115° C. at 0.07 mbar. $[\alpha]_D^{26}$=58.3° (undiluted).

Example Z32

1) tert.-Butyl 3R,4R-4-allyloxy-3-hydroxypyrrolidine-1-carboxylate

The reaction is similar to that in Example Z31, 1), but with tert.-butyl R,R-3,4-dihydroxypyrrolidine-1-carboxylate.

Boiling point: 145° C. at 0.1 mbar. $[\alpha]_D^{23}$=+9.5° (c=10 methanol) Gas chromatography reveals a 95% product.

2) tert.-Butyl 3R,4R-3-hydroxy-4-(2-hydroxyethoxy)-pyrrolidine- 1-carboxylate

The reaction is similar to that in Example Z31, 2), but with tert.-butyl 3R,4R-4-allyloxy-3-hydroxypyrrolidine-1-carboxylate.

Yield: 99% of theoretical (batch of 0.175 mol). $[\alpha]_D^{20}$= +16.5° (c=0.94, methanol).

3) 3R,4R-1-tert.- Butoxycarbonyl-3-tosyloxy-4-(2-tosyloxyethoxy)-pyrrolidine

The reaction is similar to that in Example Z31, 3), but with 0.11 mol tert.-butyl 3R, 4R-3-hydroxy-4-(2-hydroxyethoxy)-pyrrolidine- 1-carboxylate.

Yield: Quantitative

4) Tert.-butyl 1R,6S-5-benzyl-2-oxa-5,8-diazabicyclo-[4.3.0]nonane-8-carboxylate The reaction is similar to that in Example Z31, 4) but with 0.1 mol 3R,4R-1-tert.-butoxycarbonyl-3-tosyloxy-4-(2-tosyloxyethoxy)-pyrrolidine.

Yield: 40% of theoretical.

5) 1R,6S-5-Benzyl-2-oxa-5,8-diazabicyclo[4.3.0]nonane

The reaction is similar to that in Example Z31, 5), but with 40 mmol tert.-butyl 1R, 6S-5-benzyl-2-oxa-5,8-diazabicyclo[ 4.3.0]nonane-8-carboxylate Yield: 63% of theoretical Boiling point: 120° C. at 0.06 mbar. Gas chromatography reveals a 95% product. $[\alpha]_D^{23}$= +58.5° (undiluted).

Example Z33

1) 1S,6R-2-oxa-5,8-diazabicyclo[4.3.0]nonane dihydrochloride 7.5 g (34.4 mmoles) of 1S,6R-5-benzyl-2-oxa-5,8-diazabicyclo[ 4.3.0]-nonane are hydrogenated in 200 ml of ethanol with 7 ml of concentrated hydrochloric acid over 1 g of palladium (10%) on active carbon at 100° C. and 100 bar. The catalyst is suctioned off and washed several times with water. The aqueous filtrate is concentrated and the residue crystallizes. The crystals are thoroughly ground in ethanol, suctioned off, and dried in the air.

Yield: 4.6 g (66.5% of theoretical). Boiling point: 233°–235° C.

2) 1S,6R-2-oxa-5,8-diazabicyclo[4.3.0]nonane 59 g (0.27 mol) of 1S,6R-5-benzyl-2-oxa-5,8-diazabicyclo[ 4.3.0]nonane in 500 ml of ethanol are hydrogenated over 5 g of palladium (10%) on active carbon at 120° C. and 120 bar. The catalyst is suctioned off, the filtrate concentrated, and the residue distilled.

Yield: 32.9 g (95% of theoretical). Boiling point: 65° C. at 0.03 mbar. Rotation: $[\alpha]_D^{23}$=+8.2° (undiluted).

ee≧99.5% (by derivatization with Mosher's reagent).

Example Z34

1) 1R,6S-2-oxa-5,8-diazabicyclo[4.3.0]nonane dihydrochloride

The reaction is similar to that in Example Z33, 1) but with 1R,6S-5-benzyl-2-oxa-5,8-diazabicyclo[4.3.0]nonane.

Yield: 77% of theoretical (batch of 23.8 mol). Melting point: 230°–232° C.

2) 1R,6S-2-oxa-5,8-diazabicyclo[4.3.0]nonane

The reaction is similar to that in Example Z33, 2) but with R,6S-5-benzyl-2-oxa-5,8-diazabicyclo[4.3.0]nonane Yield: 93.3% of theoretical (batch of 1.58 mol). Boiling point: 63°–65° C. at 0.03 mbar. Rotation: $[\alpha]_D^{23}$=−8.4° (undiluted).

ee>99.5% (by derivatization with Mosher's reagent).

1R,6R- and 1S,6S-2-oxa-5,8-diazabicyclo[4.3.0]nonane can be similarly obtained.

Preparation of the active compounds

Example 1

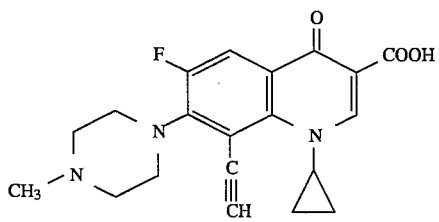

2.32 g (8 mmol) of 1-cyclopropyl-8-ethinyl-6,7-difluoro-1,4-dihydro-4-oxo-3-quinolinecarboxylic acid in a mixture of 60 ml of acetonitrile and 30 ml of dimethylformamide are refluxed for 1 hour with 0.92 g (8 mmol) of 1,4-diazabicyclo [2.2.2]octane and 1.2 g (12 mmol) of N-methylpiperazine. The suspension is concentrated, the residue is stirred with acetonitrile, and undissolved crystallisate is filtered off with suction and dried.

Yield: 1.83 g (62% of theory) of 1-cyclopropyl-8-ethinyl-6-fluoro-1,4-dihydro-7-(4-methyl-1-piperazinyl)- 4-oxo-3-quinolinecarboxylic acid.

Melting point: 228°–230° C. (with decomposition). $^1$H NMR (d$^6$-DMF): δ4.95 ppm s (—C≡C—H).

Using the products of Examples Z14, Z7 and Z9, the following are obtained analogously to Example 1:

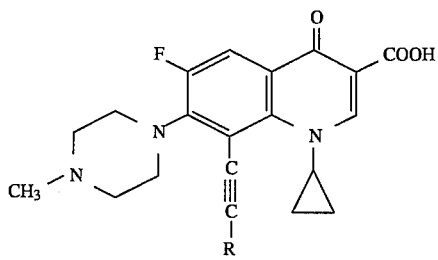

Example 2

(R=CH₃): 1-Cyclopropyl-6-fluoro-1,4-dihydro-7-(4-methyl-1-piperazinyl)-4-oxo-8-(propin-1-yl)-3-quinolinecarboxylic acid.

Melting point: 246°–249° C. (with decomposition).

Example 3

(R=CH₂CH₂CH₂CH₃): 1-Cyclopropyl-6-fluoro-8-(hexin-1-yl)-1,4-dihydro-7-(4-methyl-1-piperazinyl)-4-oxo-3-quinolinecarboxylic acid.

Melting point: 206°–208° C. (with decomposition).

Example 4

(R=C(CH₃)₃: 1-Cyclopropyl-8-(3,3-dimethylbutin-1-yl)-6-fluoro-1,4-dihydro-7-(4-methyl-1-piperazinyl)-4-oxo- 3-quinolinecarboxylic acid.

Melting point: 234°–237° C. (with decomposition).

Example 5

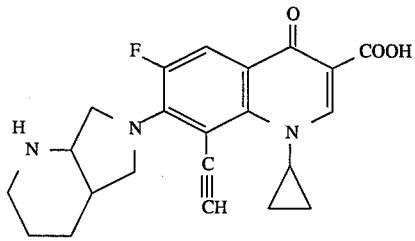

Analogously to Example 1, the reaction is carried out with cis-2,8-diazabicyclo[4.3.0]nonane to give 1-cyclopropyl-7-(cis-2,8-diazabicyclo[4.3.0]non-8-yl)-8-ethinyl- 6-fluoro-1,4-dihydro-4-oxo-3-quinolinecarboxylic acid of melting point 225°–227° C. (with decomposition). ¹H NMR (d⁶-DMF): δ 4.9 s (—C≡C—H).

Example 6

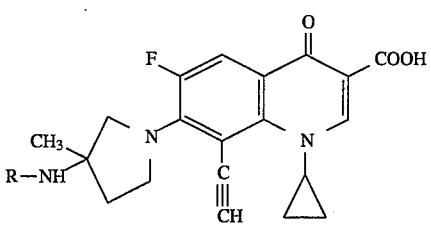

A: R = CO—O—C(CH₃)₃
B: R = H x CF₃COOH

A) Analogously to Example 1, the reaction is carried out with 3-tert.-butoxycarbonylamino-3-methylpyrrolidine to give 7-(3-tert.-butoxycarbonylamino- 3-methyl-1-pyrrolidinyl)-1-cyclopropyl-8-ethinyl-6-fluoro- 1,4-dihydro-4-oxo-3-quinolinecarboxylic acid of melting point 244°–246° C. (with decomposition). ¹H NMR (d⁶-DMSO): δ4.92 ppm s (—C≡C—H).

B) 500 mg of the product of stage A are dissolved in 5 ml of trifluoroacetic acid with ice-cooling, the solution is concentrated in vacuo, the residue is brought to crystallisation by stirring with three times approximately 1 ml portions of ethanol, and the salt is filtered off with suction, washed with ethanol and dried.

Yield: 270 mg (52% of theory) of 7-(3-amino-3-methyl-1-pyrrolidinyl)-1-cyclopropyl-8-ethinyl-6-fluoro- 1,4-dihydro-4-oxo-3-quinolinecarboxylic acid trifluoroacetate.

Melting point: 242°–244° C. (with decomposition).

Example 7

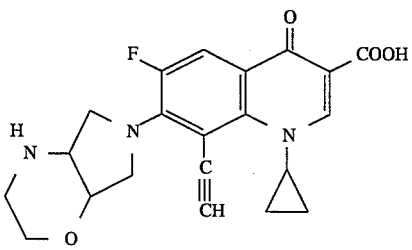

Analogously to Example 1, the reaction is carried out with 2-oxa-5,8-diazabicyclo[4.3.0]nonane to give 1-cyclopropyl-8-ethinyl-6-fluoro-1,4-dihydro-7-(2-oxa-5,8-diazabicyclo[4.3.0]non-8-yl)-4-oxo-3-quinolinecarboxylic acid of melting point 290° C. (with decomposition; sintering starts at approximately 170° C.). ¹H NMR (d⁶-DMSO ): δ5.0 ppm s (—C≡CH).

Example 8

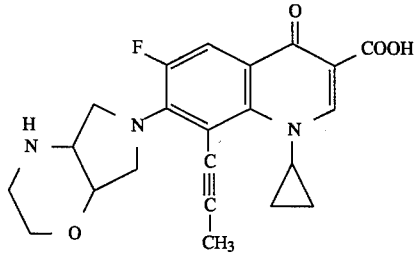

Analogously to Example 1, 2-oxa-5,8-diazabicyclo[4.3.0]nonane are reacted with the product of Example Z14 to give 1-cyclopropyl-6-fluoro-1,4-dihydro-7-(2-oxa-5,8-diazabicyclo[4.3.0]non-8-yl)-4-oxo-8-(propin-1-yl)-3-quinolinecarboxylic acid of melting point 241°–242° C. (with decomposition).

Example 9

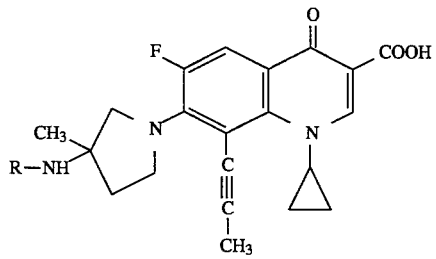

A: R = (CH₃)₃C—O—CO—
B: R = H

A) 303 mg (1 mmol) of the product of Example Z14 in a mixture of 6 ml of acetonitrile and 3 ml of dimethylformamide are treated with 240 mg of 3-tert.-butoxycarbonylamino- 3-methyl-pyrrolidine and 134 mg (1.2 mmol) of 1,4-diazabicyclo[2.2.2]octane and the mixture is refluxed for 2 hours. The mixture is concentrated in vacuo, the residue is stirred with 30 ml of water, and the mixture is dried at 80° C. in vacuo.

Yield: 420 mg (87% of theory) of 7-(3-tert.-butoxycarbonylamino- 3-methyl-1-pyrrolidinyl)-1-cyclopropyl-6-fluoro-1,4-dihydro-4-oxo-8-(propin-1-yl)-3-quinolinecarboxylic acid.

Melting point: 195°–196° C. (with decomposition). ¹H NMR (d⁶-DMSO): δ1.42 s (CH₃ on the pyrrolidine), 2.12 ppm s (CH₃—C≡C—).

B) 180 mg of the product of stage A are dissolved in 1.6 ml of trifluoroacetic acid at 0° C., and, after 1.25 hours, the solution is concentrated. The residue is purified by chromatography (silica gel, dichloromethane/methanol/17% strength aqueous ammonia=30:8:1). 10 mg of 7-(3-amino-3-methyl-1-pyrrolidinyl)- 1-cyclopropyl-6-fluoro-1,4-dihydro-4-oxo- 8-(propin-1-yl)-3-quinolinecarboxylic acid of melting point 209°–210° C. are isolated (with decomposition).

Mass spectrum: m/e 383 (M⁺), 309, 298, 267 (100%), 133, 70.

Example 10

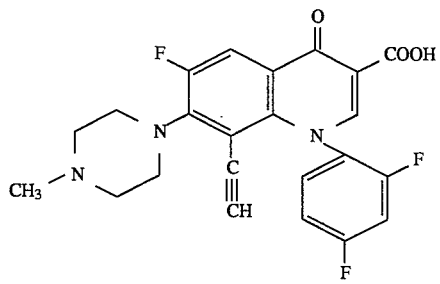

Analogously to Example 1, the product of Example Z12 is reacted with N-methylpiperazine to give 8-ethinyl-6-fluoro-1-(2,4-difluorophenyl)-1,4-dihydro-7-(4-methyl-1-piperazinyl)- 4-oxo-3-quinolinecarboxylic acid of melting point 193°–195° C. (with decomposition). ¹H NMR (CDCl₃): 3.35 s (–C≡CH).

Example 11

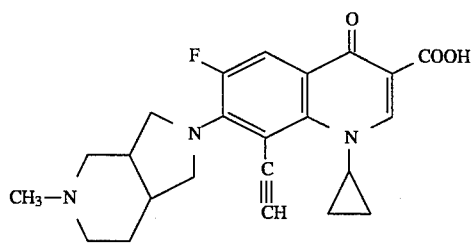

Analogously to Example 1, the reaction is carried out with 3-methyl-3,8-diazabicyclo[4.3.0]nonane, and 1-cyclopropyl- 8-ethinyl-6-fluoro-1,4-dihydro-7-(3-methyl- 3,8-diazabicyclo[4.3.0]non-8-yl)-4-oxo-3-quinoline-carboxylic acid, which is obtained as crude product, is purified by chromatography (silica gel; dichloromethane/methane/ 20% aqueous ammonia 2:4:1). ¹H NMR (CDCl₃): 4.15 s (—C≡C—H).

Example 12

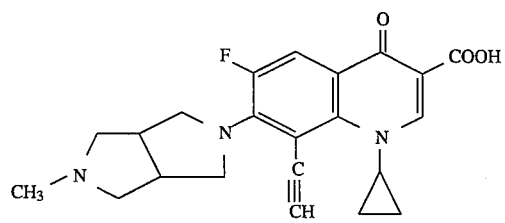

Analogously to Example 1, the reaction is carried out with 3-methyl-3,7-diazabicyclo[3.3.0]octane to give 1-cyclopropyl- 8-ethinyl-6-fluoro-1,4-dihydro-7-(7-methyl- 3,7-diazabicyclo[3.3.0]oct-3-yl)-4-oxo-3-quinolinecarboxylic acid of melting point 212°–216° C. (with decomposition). ¹H NMR (d⁶-DMF): δ4.95 s (—C≡C—H).

Example 13

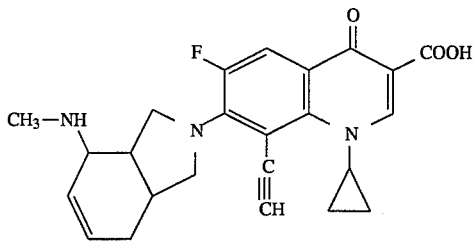

Analogously to Example 1, the reaction is carried out with 4-methylamino-1,3,3a,4,7,7a-hexahydroisoindole to give 1-cyclopropyl-8-ethinyl-6-fluoro-1,4-dihydro-7-(4-methylamino- 1,3,3a,4,7,7a-hexahydroisoindol-2-yl)-4-oxo- 3-quinolinecarboxylic acid of melting point 128°–133° C. (with decomposition). $^1$H NMR (d$^6$-DMSO): δ4.93 ppm s (—C≡CH).

Example 14

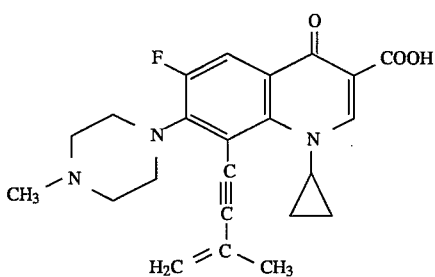

164 mg (0.5 mmol) of the product of Example Z18 are reacted analogously to Example 1 with 1-methylpiperazine to give 120 mg of 1-cyclopropyl-6-fluoro-1,4-dihydro-8-( 3-methyl-but-3-en-1-inyl)-7-(4-methyl-1-piperazinyl)-4-oxo- 3-quinolinecarboxylic acid of melting point 195°–197° C. (with decomposition) (recrystallised from glycol monomethyl ether). $^1$H NMR (CDCl$_3$): δ5.36 m (>C=CH$_2$), 2.4 s (N—CH$_3$), 2.0 t (C—CH$_3$).

Example 15

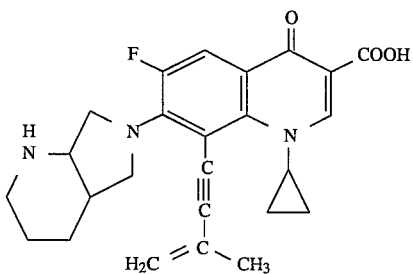

Analogously to Example 14, the reaction is carried out with 2,8-diazabicyclo[4.3.0]nonane to give 1-cyclopropyl- 7-(2, 8-diazabicyclo[4.3.0]non-8-yl)-6-fluoro-1,4-dihydro- 8-(3-methyl-but-3-en-1-inyl)-4-oxo-3-quinolinecarboxylic acid of melting point 201°–202° C. (with decomposition).

Example 16

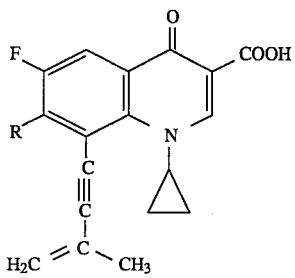

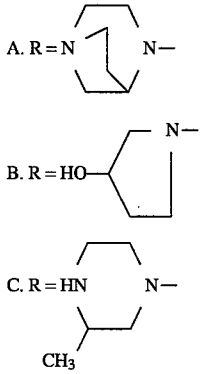

Analogously to Example 14, the reaction is carried out with
A. 1,4-Diazabicyclo[3.2.1]octane
B. 3-Hydroxypyrrolidine
C. 2-Methylpiperazine
to give the following compounds:
A. 1-Cyclopropyl-7-(1,4-diazabicyclo[3.2.1]oct-4-yl)-6-fluoro- 1,4-dihydro-8-(3-methyl-but-3-en-1-inyl)-4-oxo- 3-quinolinecarboxylic acid,
B. 1-Cyclopropyl-6-fluoro-1,4-dihydro-7-(3-hydroxy-1-pyrrolidinyl)- 8-(3-methyl-but-3-en-1-inyl)-4-oxo-3-quinolinecarboxylic acid, melting point: 190°–198° C. (with decomposition),
C. 1-Cyclopropyl-6-fluoro-1,4-dihydro-8-(3-methyl-but-3-en-1-inyl)-7-(3-methyl-1-piperazinyl)-4-oxo-3-quinolinecarboxylic acid.

Example 17

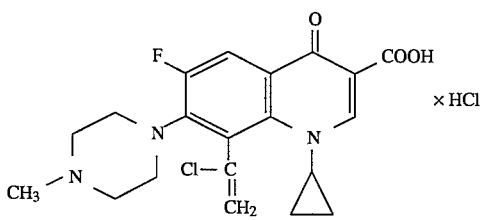

100 mg of the product of Example 1 are dissolved in 40 ml of 1N hydrochloric acid, and the solution is stirred for 2 hours at 30° C. This gives a suspension which is concentrated. The residue is stirred with a little isopropanol, and the precipitate is filtered off with suction, washed with isopropanol and dried in vacuo at 90° C.

Yield: 0.1 g (83% of theory) of 8-(1-chlorovinyl)-1-cyclopropyl- 6-fluoro-1,4-dihydro-7-(4-methyl-1-piperazinyl)- 4-oxo-3-quinolinecarboxylic acid hydrochloride.

Melting point: 251°–252° C. (with decomposition).

$^1$H NMR (d$^6$-DMSO): δ6.0 ppm dd (—C=CH$_2$).

Example 18

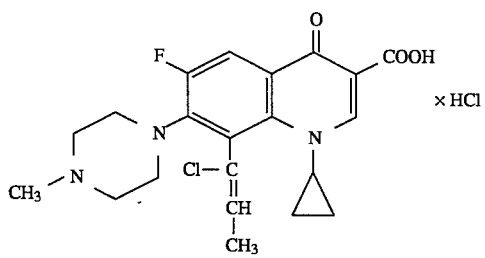

A) 100 mg of the product of Example 2 in 58 ml of 4N hydrochloric acid are heated for 5 hours at 60° C. The mixture is concentrated, and the residue is stirred with diethyl ether and dried in vacuo at 70° C.

Yield: 90 mg of cis-trans-8-(1-chloro-1-propenyl)-1-cyclopropyl- 6-fluoro-1,4-dihydro-7-(4-methyl-1-piperazinyl)- 4-oxo-3-quinolinecarboxylic acid hydrochloride.

Melting point: 235°–237° C. (with decomposition).

Mass spectrum: m/e 419 (M$^+$), 71, 58 (100%), 43, 36.

$^1$H NMR (d$^6$-DMSO): δ6.12 q and 6.35 q

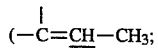
(—C=CH—CH$_3$;

two signals for cis-trans forms).

B) Analogously, cis-trans-8-(1-chloro-1-hexenyl)-1-cyclopropyl- 6-fluoro-1,4-dihydro-7-(4-methyl-1-piperazinyl)- 4-oxo-3-quinolinecarboxylic acid hydrochloride is formed with the product of Example 3.

Mass spectrum: m/e 461 (M$^+$), 425 (M-HCl), 71, 58 (100%), 43, 36.

Example 19

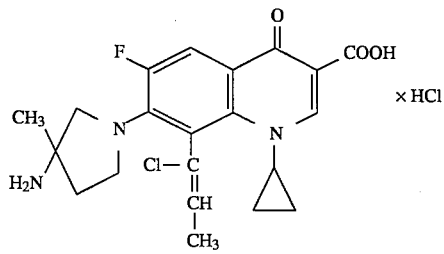

370 mg of the product of Example 10A are dissolved in 9 ml of half-concentrated hydrochloric acid, and the solution is concentrated under a high vacuum.

Yield: 340 mg of cis-trans-7-( 3-amino-3-methyl-1-pyrrolidinyl)- 8-(1-chloro-1-propenyl)-1-cyclopropyl-6-fluoro-1,4-dihydro-4-oxo-3-quinolinecarboxylic acid hydrochloride.

$^1$H NMR (d$^6$-DMSO): δ6.19 q and 6.36 q (>C=CH—CH$_3$; 2 signals for cis-trans forms).

Example 20

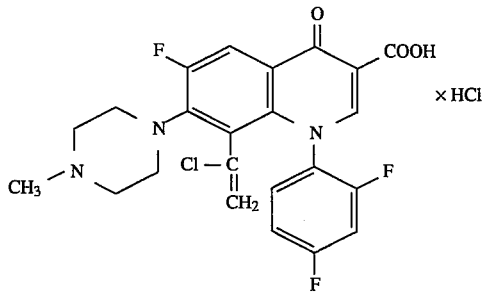

10 mg of the product of Example 10 in 4.5 ml of 2.5N hydrochloric acid are heated for 1 hour at 60° C. The mixture is concentrated, and 8-(1-chlorovinyl)-6-fluoro- 1-(2,4-difluorophenyl)-1,4-dihydro-7-(4-methyl-1-piperazinyl)- 4-oxo-3-quinolinecarboxylic acid hydrochloride is obtained as residue.

Mass spectrum: m/e 477 (M$^+$), 442 (M$^+$-Cl), 36 (100%, HCl).

Example 21

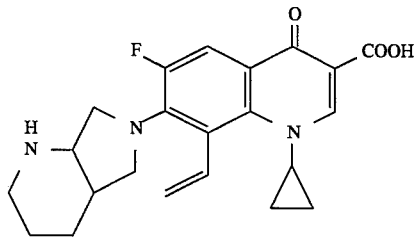

145 mg (0.5 mmol) of the product of Example Z2 in a mixture of 10 ml of acetonitrile and 5 ml of dimethylformamide are treated with 60 mg (0.54 mmol) of 1,4diazabicyclo[ 2.2.2]octane and 140 mg (1.1 mmol) of cis- 2,8-diazabicyclo[4.3.0]nonane, and the mixture is refluxed for 4 hours. The solution is concentrated, the concentrate is stirred with approximately 5 ml of water, and the mixture is brought to pH 7 using dilute hydrochloric acid. The precipitate is filtered off with suction, washed with water and dried in vacuo at 90° C.

Yield: 120 mg (61% of theory) of 1-cyclopropyl-7-(cis-2,8-diazabicyclo[4.3.0]non-8-yl)-6-fluoro-1,4-dihydro-4-oxo- 8-vinyl-3-quinolinecarboxylic acid.

Melting point: 205°–207° C. (with decomposition). $^1$H NMR (CF$_3$COOD): δ5.05 d (1H), 5.7 d (1H), 7.55 dd (1H) (signal groups for —CH=CH$_2$).

Example 22

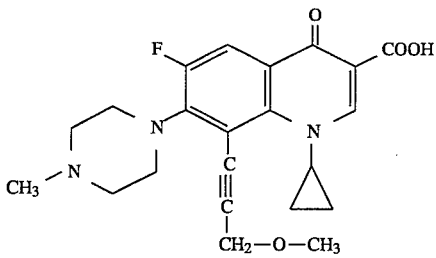

Analogously to Example 1, the reaction is carried out with the product of Example Z26, and 1-cyclopropyl-6-fluoro-1,4-dihydro-7-(4-methyl-1-piperazinyl)-8-(3-methoxy-propin-1-yl)-4-oxo-3-quinolinecarboxylic acid of melting point 187°–189° C. is obtained. $^1$H NMR (CDCl$_3$): δ8.95 s (1H), 8 d (1H), 4.37 s (O—CH$_2$), 4.35 m (1H), 3.58 m (4H), 3.43 s (O—CH$_3$), 2.58 m (4H), 2.38 s (N—CH$_3$), 1.33 m (2 H), 1.02 ppm m (2H).

Example 23

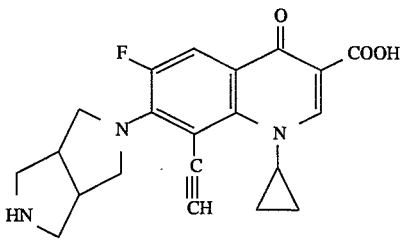

Analogously to Example 1, the reaction is carried out with 3,7-diazabicyclo[3.3.0]octane, the reaction product is chromatographed on silica gel using dichloromethane/methanol/17% strength ammonia (30:8:1) as the eluent, and 1-cyclopropyl-7-(3,7-diazabicyclo[3.3.0]oct-3-yl)-8-ethinyl-6-fluoro-1,4-dihydro-4-oxo-3-quinolinecarboxylic acid is obtained as a "solidified foam". $^1$H NMR (d$^6$-DMSO): δ4.9 s (—C≡CH).

Example 24

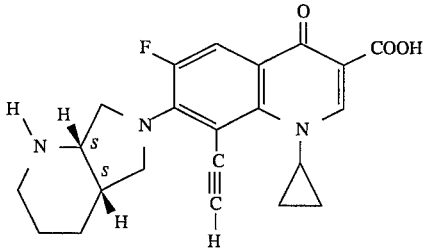

5.4 g (18.7 mmol) of 1-cyclopropyl-8-ethinyl-6,7-difluoro-1,4-dihydro-4-oxo-3-quinoline-carboxylic acid in a mixture of 180 ml of acetonitrile and 90 ml of dimethylformamide are refluxed with 2.16 g (19.3 mmol) of 1,4-diazabicyclo[2.2.2]octane and 3.2 g (25.4 mmol) of S,S-2,8-diazabicyclo[4.3.0]nonane for 1 hour. The suspension is chilled in ice and the precipitate suctioned off, mixed with 50 ml of water, and dried in a high vacuum at 100° C.

Yield: 5.3 g (72% of theoretical) of 1-cyclopropyl-7-(S,S-2,8-diazabicyclo[4.3.0]non-8-yl)-8-ethinyl-6-fluoro-1,4-dihydro-4-oxo-3-quinoline-carboxylic acid.

Melting point: 224°–226° C. (accompanied by decomposition). $[\alpha]_D^{23}$=–38° (c=0.5; DMF).

Example 25

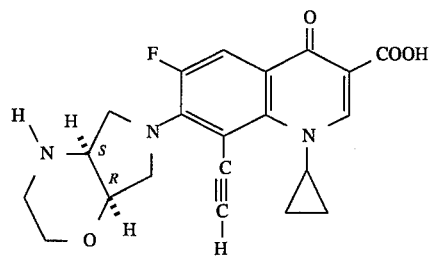

The reaction is similar to that in Example 24 but with 1R,6S-2-oxa-5,8-diazabicyclo 4.3.0]nonane, resulting in a yield of 75.6% 1-cyclopropyl-8-ethinyl-6-fluoro-1,4-dihydro-7-(1R,6S-2-oxa-5,8-diazabicyclo[4.3.0]non-8-yl)-4-oxo-3-quinoline-carboxylic acid.

Melting point: 214–216° C. (accompanied by decomposition). $[\alpha]_D^{23}$: –67° (c=0.5; CHC$_3$).

Example 26

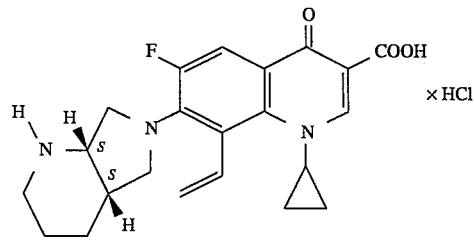

A. As in Example 24, conversion to 1-cyclopropyl-7-(S,S-2,8-diazabicyclo[4.3.0]non-8-yl)-6-fluoro-1,4-dihydro-4-oxo-8-vinyl-3-quinoline carboxylic acid with a melting point of 188°–190° C. (accompanied by decomposition) by heating for 30 hours with 1-cyclopropyl-6,7-difluoro-1,4-dihydro-4-oxo-8-vinyl-3-quinoline-carboxylic acid is carried out.

B. 1 g of the betaine from step A is dissolved in 7 ml of 6n hydrochloric acid. The solution is filtered through glass and concentrated. The viscous residue is induced to crystallize by mixing with ethanol and methylene chloride, suctioned off, and dried.

Yield: 0.59 g (54% of theoretical) of 1-cyclopropyl-7-(S,S-2,8-diazabicyclo[4.3.0]-non-8-yl)-6-fluoro-1,4-dihydro-4-oxo-8-vinyl-3-quinoline-carboxylic acid hydrochloride.

Melting point: >170° C. with decomposition. $[\alpha]_D^{23}$: –97° C. (c=0.47, water).

We claim:

1. Quinolonecarboxylic acid compounds of the formula (I)

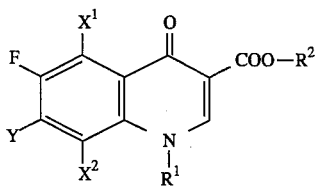

in which
- $R^1$ represents straight-chain or branched $C_1$–$C_4$-alkyl which is optionally substituted by hydroxyl, halogen or $C_1$–$C_3$-alkoxy, or represents optionally halogen- or $C_1$–$C_3$-alkyl-substituted $C_3$–$C_6$-cycloalkyl, $C_2$–$C_4$ alkenyl, or $R^1$ furthermore represents $C_1$–$C_3$-alkoxy, amino, monoalkylamino having 1 to 3 C atoms, dialkylamino having 2 to 6 C atoms, or phenyl which is optionally monosubstituted to trisubstituted by halogen,
- $R^2$ represents hydrogen, alkyl having 1 to 4 carbon atoms or (5-methyl-2-oxo-1,3-dioxol-4-yl)-methyl,
- $X^1$ represents hydrogen, fluorine, chlorine, amino or methyl,
- $X^2$ represents ethinyl,
- Y represents

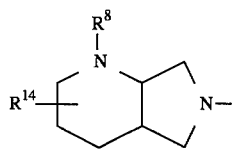

- $R^8$ represents hydrogen or methyl,
- $R^{14}$ represents hydrogen or methyl, or their pharmaceutically acceptable hydrates and acid addition salts or the alkali metal salts, alkaline earth metal salts, silver salts and guanidinium salts.

2. Quinolonecarboxylic acid derivatives according to claim 1, where
- $R^1$ represents optionally hydroxyl-substituted $C_1$–$C_2$-alkyl, $C_3$–$C_3$-cycloalkyl, vinyl, amino, monoalkylamino having 1 to 2 atoms, dialkylamino having 2 to 4 C atoms, or phenyl which is optionally monosubstituted or disubstituted by halogen, and
- $R^2$ represents hydrogen, alkyl having 1 to 3 carbon atoms or (5-methyl-2-oxo-1,3-dioxol-4-yl)-methyl.

3. Quinolonecarboxylic acid derivatives according to claim 1, where
- $R^1$ represents methyl, ethyl, cyclopropyl or phenyl which is optionally monosubstituted or disubstituted by fluorine, and
- $R^2$ represents hydrogen, methyl or ethyl.

4. A compound according to claim 1 selected from the group consisting of
1-cyclopropyl-7-(cis-2,8-diazabicyclo[4.3.0.]non-8-yl)-8-ethinyl- 6-fluoro-1,4-dihydro-4-oxo-3-quinolinecarboxylic acid,
pharmaceutically acceptable hydrates thereof, acid addition salts thereof, alkali-metal salts thereof, alkali-earth-metal salts thereof, silver salts thereof, and guanidinium salts thereof.

5. The compound 1-cyclopropyl-7-(1S,6S-2,8-diazabicyclo[ 4.3.0]non-8-yl)-8-ethinyl-6-fluoro-1,4-dihydro-4-oxo- 3-quinoline-carboxylic acid.

6. An antibacterial composition comprising an antibacterially-effective amount of a compound according to claim 1 and a diluent.

7. A composition according to claim 6, in the form of a tablet, capsule, or ampule.

8. A composition according to claim 6, wherein the diluent comprises an animal feedstock.

9. A method of combating bacteria in a patient in need thereof, which comprises administering to such patient an antibacterially-effective amount of a compound according to claim 1.

10. A method of promoting the growth of an animal, which comprises administering to said animal a growth-promoting-effective amount of a compound according to claim 1.

* * * * *

UNITED STATES PATENT AND TRADEMARK OFFICE
CERTIFICATE OF CORRECTION

PATENT NO. : 5,468,742
DATED : November 21, 1995
INVENTOR(S) : Petersen, et al.

It is certified that error appears in the above-indentified patent and that said Letters Patent is hereby corrected as shown below:

| | |
|---|---|
| Title Page & Col 1 line 2 | [54] Invention: Delete " 9-ETHINYL " and substitute -- 8-ETHINYL -- |
| Col. 54, line 1 | Delete " $C_3$-$C_3$-cycloalkyl " and substitute -- $C_3$-$C_5$-cycloalkyl -- |
| Col. 54, line 2 | After " 1 to 2 " insert -- C -- |

Signed and Sealed this

Twenty-eighth Day of May, 1996

Attest:

BRUCE LEHMAN

*Attesting Officer*  *Commissioner of Patents and Trademarks*